(12) United States Patent
Shima et al.

(10) Patent No.: US 11,150,253 B2
(45) Date of Patent: Oct. 19, 2021

(54) METHOD FOR ANALYZING BLOOD SPECIMEN, REAGENT AND REAGENT KIT FOR ANALYZING BLOOD SPECIMEN, AND BLOOD SPECIMEN ANALYZER

(71) Applicants: SYSMEX CORPORATION, Kobe (JP); PUBLIC UNIVERSITY CORPORATION NARA MEDICAL UNIVERSITY, Kashihara (JP)

(72) Inventors: Midori Shima, Kashihara (JP); Keiji Nogami, Kashihara (JP); Tomoko Matsumoto, Kashihara (JP); Sho Shinohara, Kobe (JP); Nobuo Arai, Kobe (JP)

(73) Assignees: SYSMEX CORPORATION, Kobe (JP); PUBLIC UNIVERSITY CORPORATION NARA MEDICAL UNIVERSITY, Kashihara (JP)

( * ) Notice: Subject to any disclaimer, the term of this patent is extended or adjusted under 35 U.S.C. 154(b) by 0 days.

(21) Appl. No.: 15/498,746

(22) Filed: Apr. 27, 2017

(65) Prior Publication Data

US 2017/0315142 A1 Nov. 2, 2017

(30) Foreign Application Priority Data

Apr. 28, 2016 (JP) .............................. JP2016-090860

(51) Int. Cl.
| | |
|---|---|
| *G01N 33/86* | (2006.01) |
| *G01N 21/27* | (2006.01) |
| *G01N 21/82* | (2006.01) |
| *G01N 33/49* | (2006.01) |

(52) U.S. Cl.
CPC ........... *G01N 33/86* (2013.01); *G01N 21/272* (2013.01); *G01N 21/82* (2013.01); *G01N 33/4905* (2013.01)

(58) Field of Classification Search
CPC ...... G01N 33/86; G01N 21/272; G01N 21/82; G01N 33/4905
USPC .......................................................... 435/13
See application file for complete search history.

(56) References Cited

U.S. PATENT DOCUMENTS

| | | |
|---|---|---|
| 2007/0002309 A1 | 1/2007 | Yamamoto |
| 2008/0268483 A1 | 10/2008 | Goldenberg et al. |
| 2013/0065260 A1 | 3/2013 | Grunzke et al. |
| 2013/0344519 A1 | 12/2013 | Leong et al. |
| 2014/0186865 A1 | 7/2014 | Amiral |
| 2015/0240287 A1 | 8/2015 | Soeda et al. |
| 2017/0234853 A1 | 8/2017 | Contant et al. |

FOREIGN PATENT DOCUMENTS

| | | |
|---|---|---|
| CN | 101184775 A | 5/2008 |
| CN | 103946390 A | 7/2014 |
| CN | 104937423 A | 9/2015 |
| EP | 2 677 037 A1 | 12/2013 |
| EP | 2 775 292 A1 | 9/2014 |
| EP | 3 076 173 A1 | 10/2016 |
| JP | 2008-531692 A | 8/2008 |
| JP | 2013-205087 A | 10/2013 |
| WO | 2006/072602 A1 | 7/2006 |
| WO | 2006/096345 A2 | 9/2006 |
| WO | 2013/190071 A2 | 12/2013 |
| WO | 2015171116 A1 | 11/2015 |
| WO | 2016/012729 A1 | 1/2016 |
| WO | 2016019145 A1 | 2/2016 |

OTHER PUBLICATIONS

Communication dated Feb. 12, 2020, from the Japanese Patent Office in Application No. 2016-090860.
Chinese Office Action dated Jun. 19, 2020 in a counterpart Chinese patent application No. 201710290121.8.
Communication dated Nov. 4, 2020 from the European Patent Office in Application No. 17168386.5.
Japanese Office Action dated Aug. 18, 2020 in a counterpart Japanese patent application No. 2016-090860.
Communication dated Mar. 30, 2021, from the Japanese Patent Office in Application No. 2016-090860.
Communication dated Apr. 27, 2021, issued by the State Intellectual Property Office of the P.R.C. in application No. 201710290121.8.

*Primary Examiner* — Jennifer M. H. Tichy
(74) *Attorney, Agent, or Firm* — Sughrue Mion, PLLC

(57) ABSTRACT

Disclosed is a method for analyzing a blood specimen, including the steps of: coagulating a blood specimen in the presence of an activating agent for fibrinolytic system to acquire a coagulation waveform; and acquiring information about fibrinolytic capacity of the blood specimen based on the acquired coagulation waveform.

14 Claims, 21 Drawing Sheets

METHOD FOR ANALYZING BLOOD SPECIMEN, REAGENT AND REAGENT KIT FOR ANALYZING BLOOD SPECIMEN, AND BLOOD SPECIMEN ANALYZER

CROSS REFERENCE TO RELATED APPLICATIONS

This application claims priority from prior Japanese Patent Application No. 2016-090860, filed on Apr. 28, 2016, entitled "METHOD FOR ANALYZING BLOOD SPECIMEN, REAGENT AND REAGENT KIT FOR ANALYZING BLOOD SPECIMEN, AND BLOOD SPECIMEN ANALYZER", the entire contents of which are incorporated herein by reference.

TECHNICAL FIELD

The present invention relates to a method for analyzing a blood specimen. The present invention also relates to a reagent and a reagent kit for analyzing a blood specimen. Furthermore, the present invention also relates to a blood specimen analyzer.

BACKGROUND

In vivo, if blood clots (fibrin clots) are developed in blood vessels or tissues by hemostasis or any pathologic factor, fibrinolysis reaction occurs to remove them. In the fibrinolysis reaction, fibrinolytic system composed of a plasminogen activator (PA) and plasmin plays a major role. Specifically, plasminogen, which is the precursor of plasmin, is activated by PA to be plasmin, and the plasmin decomposes fibrin in blood clots to remove the blood clots. There are factors regulating the fibrinolytic system in vivo. For example, a plasminogen activator inhibitor (PAI) inhibits activation of plasminogen caused by PA. α2-antiplasmin (α2AP; also referred to as α2-plasmin inhibitor) suppressively regulates enzymatic activity of plasmin on fibrin.

When the fibrinolytic system has any abnormality, a bleeding tendency or blood clot formation are promoted. For example, a bleeding tendency is observed in a patient having a deficiency in PAI-1, which is a kind of PAI. In a patient having a deficiency in α2AP, bleeding temporarily stops after being externally injured, but there is a bleeding tendency that re-bleeding occurs because of too fast dissolution of blood clots. Patients with plasminogen abnormality or deficiency are at risk of developing thrombosis, because plasminogen activity is low and the fibrinolytic system does not sufficiently work.

Examination of the fibrinolytic system is composed mainly of measurements of the antigen amount (protein amount) and activity of the related factors. For example, in the measurement of plasminogen activity, plasminogen in a specimen is activated by streptokinase, and then reacted with a chromogenic synthetic substrate, and the plasminogen activity is measured from the amount of liberated dye. By using a calibration curve, the protein amount in plasminogen can be calculated from the activity value. U.S. Application Publication No. 2013/0065260 discloses that two fluorescent synthetic substrates each specific to thrombin and plasmin, a tissue-type plasminogen activator, and a tissue factor are added to blood plasma and reacted with one another, and the amount and rate of thrombin and plasmin formed are measured based on the fluorescence intensity caused from the decomposed fluorescent synthetic substrate.

Conventional examination of the fibrinolytic system only measures enzymatic activity to a synthetic substrate, so that it hardly reflects the state of the fibrinolysis reaction occurring in vivo. The simultaneous formation test of thrombin and plasmin described in U.S. Application Publication No. 2013/0065260 can comprehensively analyze coagulation and fibrinolysis, but this analysis is also based on enzymatic activity to a synthetic substrate. In addition, a long time around 2 to 4 hours is necessary for obtaining the results. Therefore, the development of a means allowing quick analysis of the state more similar to in vivo fibrinolysis reaction is desired.

SUMMARY OF INVENTION

The scope of the present invention is defined solely by the appended claims, and is not affected to any degree by the statements within this summary.

The inventors have found that the state more similar to in vivo fibrinolysis reaction can be quickly analyzed by a novel approach of analyzing a series of the steps from blood coagulation through fibrinolysis by a coagulation waveform, and thus have accomplished the present invention.

A first aspect of the present invention provides a method for analyzing a blood specimen. The analysis method includes the steps of: coagulating a blood specimen in the presence of an activating agent for fibrinolytic system to acquire a coagulation waveform; and acquiring information about fibrinolytic capacity of the blood specimen based on the acquired coagulation waveform.

A second aspect of the present invention provides a reagent for analyzing a blood specimen, the reagent including an activating agent for fibrinolytic system and a reagent for measuring a coagulation time.

A third aspect of the present invention provides a reagent kit for analyzing a blood specimen, the kit including first and second reagents. In the reagent kit, the first reagent contains an activating agent for coagulation system, and the second reagent contains an activating agent for fibrinolytic system as well as calcium ions, or, the first reagent contains an activating agent for coagulation system and an activating agent for fibrinolytic system, and the second reagent contains calcium ions.

A fourth embodiment of the present invention provides a reagent kit for analyzing a blood specimen, the kit including first, second, and third reagents. In the reagent kit, the first reagent contains an activating agent for coagulation system, the second reagent contains an activating agent for fibrinolytic system, and the third reagent contains calcium ions.

A fifth embodiment of the present invention provides a blood specimen analyzer. The analyzer includes a measuring sample preparation unit for preparing a measuring sample including a blood specimen, an activating agent for fibrinolytic system, a reagent for measuring a coagulation time, and calcium ions; an information acquisition unit for acquiring a coagulation waveform from the prepared measuring sample; and a control unit. The control unit controls the measuring sample preparation unit so as to prepare a measuring sample from a blood specimen, an activating agent for fibrinolytic system, a reagent for measuring a coagulation time, and calcium ions, and outputs information about fibrinolytic capacity of the blood specimen based on the coagulation waveform.

DETAILED DESCRIPTION OF THE PREFERRED EMBODIMENTS

[1. Method for Analyzing Blood Specimen]

Figure 1A:
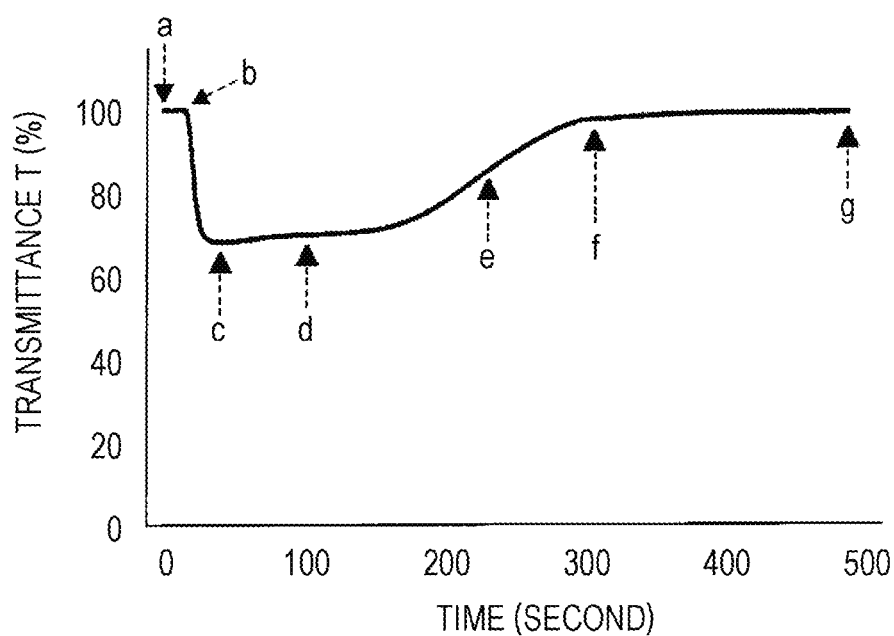
FIG. 1A is an example of a coagulation waveform obtained by measuring the transmittance of a measuring sample containing normal blood plasma, an activating agent for fibrinolytic system, a reagent for measuring a coagulation time, and calcium ions.

In a method for analyzing a blood specimen according to the first aspect (hereinafter may be referred to simply as "method"), first, a blood specimen is coagulated in the presence of an activating agent for fibrinolytic system to obtain a coagulation waveform. The coagulation waveform can be acquired from, for example, a measuring sample including a blood specimen, an activating agent for fibrinolytic system, a reagent for measuring a coagulation time, and calcium ions.

The blood specimen may be whole blood or blood plasma, and is preferably blood plasma. The blood specimen may contain a known anticoagulant that is commonly used for a coagulation test. Examples of the anticoagulant include trisodium citrate. Before the preparation of the measuring sample, the blood specimen may be warmed in advance to a temperature suitable for coagulation reaction (for example, 36° C. or higher and 38° C. or lower).

The activating agent for fibrinolytic system is not particularly limited as long as it is a substance activating plasminogen. Examples of the activating agent include tissue-type plasminogen activator (t-PA), urokinase-type plasminogen activator (u-PA), and streptokinase. These activating agents for fibrinolytic system may be used alone, or in combination of two or more of them. The t-PA, u-PA, and streptokinase may be naturally occurring proteins, or recombinant proteins. t-PA or u-PA that is commercially available as a blood clot solubilizer may be used. In a preferred embodiment, t-PA is used as the activating agent for fibrinolytic system.

In the method of the present embodiment, it is preferred that fibrinolysis starts after completion of coagulation in the measuring sample in order to analyze the state more similar to in vivo fibrinolysis reaction. For this purpose, the final concentration of the activating agent for fibrinolytic system in the measuring sample should be appropriately adjusted. The final concentration can be routinely determined by acquiring a coagulation waveform of the measuring sample. For example, when t-PA is used as the activating agent for fibrinolytic system, the final concentration of t-PA in the measuring sample is 0.1 µg/mL or more and 10 µg/mL or less, preferably 0.3 µg/mL or more and 5 µg/mL or less, and more preferably 0.5 µg/mL or more and 3 µg/mL or less.

In the method of the present embodiment, a reagent for measuring a coagulation time is used for coagulating a blood specimen. The reagent for measuring a coagulation time should be a reagent for measuring a coagulation time based on the measurement principle known in the art. Examples of the reagent include reagents for measuring at least one of prothrombin time, activated partial thromboplastin time, dilute prothrombin time, dilute activated partial thromboplastin time, kaolin coagulation time, dilute Russell's viper venom time, thrombin time, and dilute thrombin time. A commercially available reagent or reagent kit for measuring a coagulation time may be used.

The reagent for measuring a coagulation time preferably contains an activating agent for coagulation system. The activating agent for coagulation system should be a substance which activates any of coagulation factors involved in the coagulation system. Examples of the activating agent for coagulation system include ellagic acid, silica, kaolin, celite, a tissue factor, thrombin, and snake venom. The ellagic acid may be in the form of a chelate with a metal ion. The tissue factor may be from rabbit brain or human placenta, or a recombinant tissue factor. Examples of the snake venom include Russell's viper venom, Textarin snake venom, and Ecarin snake venom. These activating agents for coagulation system may be used alone, or in combination of two or more of them. Usually, commercially available reagents and reagent kits for measuring a coagulation time contain any of the activating agents for coagulation system according to the type of the coagulation time to be measured.

The final concentration of the activating agent for coagulation system in the measuring sample may be determined as appropriate according to the type of the activating agent for coagulation system. When the activating agent for coagulation system is ellagic acid, the final concentration of the ellagic acid in the measuring sample is usually 3.5 µM or more and 150 µM or less, preferably 10 µM or more and 50 µM or less. When the activating agent for coagulation system is a tissue factor, the final concentration of the tissue factor in the measuring sample is usually 0.4 µg/mL or more and 0.7 µg/mL or less, and preferably 0.5 µg/mL or more and 0.6 µg/mL or less.

The reagent for measuring a coagulation time may further contain phospholipid, because phospholipid accelerates the coagulation reaction. Examples of the phospholipid include phosphatidylethanolamine (PE), phosphatidylcholine (PC), and phosphatidylserine (PS). In the present embodiment, the reagent for measuring a coagulation time may contain one, preferably two, more preferably all of phospholipids selected from PE, PC, and PS. The phospholipid may be a naturally occurring phospholipid, or a synthetic phospholipid. Among them, a synthetic phospholipid or a naturally occurring phospholipid purified to have a purity of 99% or more is preferred. The fatty acid side chain of PE, PC, and PS is not particularly limited, and examples thereof include palmitic acid, oleic acid, and stearic acid. Among them, oleic acid is preferred. In the present embodiment, the phospholipid is preferably in the form of a liquid dissolved in an appropriate solvent.

The final concentration of the phospholipid in the measuring sample may be determined as appropriate according to the type of the phospholipid. When the phospholipid is PE, the final concentration of the phospholipid in the measuring sample is usually 1 µg/mL or more and 150 µg/mL or less, and preferably 5 µg/mL or more and 50 µg/mL or less. When the phospholipid is PC, the final concentration of the phospholipid in the measuring sample is usually 1 µg/mL or more and 100 µg/mL or less, and preferably 5 µg/mL or more and 80 µg/mL or less. When the phospholipid is PS, the final concentration of the phospholipid in the measuring sample is usually 0.1 µg/mL or more and 50 µg/mL or less, and preferably 1 µg/mL or more and 10 µg/mL or less. When two or more phospholipids are used, the total concentration of the phospholipids in the measuring sample is usually 5 µg/mL or more and 400 µg/mL or less, and preferably 20 µg/mL or more and 100 µg/mL or less.

In the present embodiment, it is preferred that the reagent for measuring a coagulation time containing a phospholipid and an activating agent for coagulation system be used. An example of the reagent for measuring a coagulation time includes a reagent for measuring an activated partial thromboplastin time (APTT). In this case, the activating agent for coagulation system is preferably a substance activating a contact factor of the intrinsic coagulation pathway, and examples of the substance include ellagic acid, silica, kaolin, and celite.

The calcium ions are necessary for initiating blood coagulation in the measuring sample. In the present embodiment, calcium ions are supplied to the measuring sample through the use of an aqueous solution containing calcium ions for preparation of the measuring sample. The aqueous solution containing calcium ions is preferably an aqueous solution of a calcium salt, and examples thereof include an aqueous calcium chloride solution and an aqueous calcium lactate solution. The calcium ion content in the measuring sample should be an amount sufficient for causing coagulation, and is, for example, usually 2 mM or more and 20 mM or less, preferably 4 mM or more and 10 mM or less in terms of the calcium chloride concentration. The aqueous solution containing calcium ions may be hereinafter referred to as "calcium solution".

Since coagulation starts upon the addition of a calcium solution, it is preferred that the calcium solution be added at the end of the preparation of the measuring sample. The measuring sample is prepared in the following manner. First, a blood specimen, an activating agent for fibrinolytic system, and a reagent for measuring a coagulation time are mixed, and then the resulting mixture is mixed with a calcium solution to prepare a measuring sample. Alternatively, first, a blood specimen and a reagent for measuring a coagulation time are mixed, and then the resulting mixture, an activating agent for fibrinolytic system, and a calcium solution are mixed to prepare a measuring sample. When a commercially available reagent for measuring a prothrombin time (PT) is used, the reagent contains a tissue factor and calcium ions, so that a measuring sample can be prepared by mixing a blood specimen, an activating agent for fibrinolytic system, and the reagent for measuring PT. The procedure used for the preparation of the measuring sample should be chosen according to the reagent for measuring a coagulation time to be used.

In the present embodiment, before the addition of the calcium solution, the above-described mixture may be incubated under conditions suitable for the coagulation reaction. For example, incubation is carried out at a temperature of 35° C. or higher and 40° C. or lower for 2 minutes or more and 5 minutes or less. The measuring sample may be prepared by hand or a full automatic measuring apparatus. Examples of the apparatus include CS Series of full automatic blood coagulation measuring apparatuses (Sysmex Corporation).

When the reagent for measuring a coagulation time containing a phospholipid and an activating agent for coagulation system is used, the measuring sample is preferably prepared as follows. First, a blood specimen is mixed with the reagent for measuring a coagulation time containing a phospholipid and an activating agent for coagulation system. Secondly, the resulting mixture is mixed with a calcium solution containing an activating agent for fibrinolytic system. In this case, the activating agent for fibrinolytic system is previously added to the calcium solution.

In the method of the present embodiment, the measuring sample prepared as described above is measured for a coagulation waveform. The coagulation waveform is a waveform showing a time-dependent change in the optical properties or physical properties of a blood specimen caused by the progress of coagulation of the specimen. In the present embodiment, the coagulation waveform may be acquired by an optical measurement method, or a physical measurement method. An example of the optical measurement method includes a method of acquiring optical information such as transmittance by irradiating the measuring sample with light. An example of the physical measurement method includes a method of acquiring physical information such as viscosity of the measuring sample by using steel balls. The measurement may be carried out by a full automatic measuring apparatus. For example, CS series of full automatic blood coagulation measuring apparatuses (Sysmex Corporation) can acquire optical information such as transmittance, and STA Compact (Roche Diagnostics K.K.), which is a full automatic blood coagulation fibrinolysis measuring apparatus, can acquire physical information such as viscosity.

The measurement conditions are not particularly limited, but the acquisition of optical information or physical information is preferably carried out continuously or intermittently during the period from the preparation of the measuring sample (specifically the time of addition of the calcium solution) through completion of fibrinolysis. Based on the optical information or physical information that is continuously or intermittently acquired during a series of steps from coagulation through fibrinolysis, the below-described parameters regarding differentiation of the coagulation waveform can be acquired in any time point or time during the steps.

The measurement time should be usually determined within the range of 10 seconds or more and 1800 seconds or less, preferably 15 seconds or more and 500 seconds or less. In the method of the present embodiment, when normal blood plasma (blood plasma obtained from a healthy subject) is used as a blood specimen, usually, fibrinolysis finishes within 400 seconds from the preparation of the measuring sample.

The coagulation waveform is preferably acquired from the optical information obtained by irradiating the measuring sample with light. Examples of the optical information include scattered light amount, transmittance, and absorbance that are continuously or intermittently measured. In this case, the coagulation waveform shows a time-dependent change in the scattered light amount, transmittance, or absorbance. The light applied to the measuring sample may be light commonly used for the measurement of a coagulation time, and examples thereof include light having a wavelength in the vicinity of 660 nm, preferably 660 nm. The light source is not particularly limited, and examples thereof include a luminescence diode and halogen lamp.

The coagulation waveform acquired in the present embodiment includes a curve itself of the coagulation waveform, and date of plots constituting the coagulation waveform. Examples of the data of plots constituting the coagulation waveform include a time from the initiation point of measurement, and measurement values of optical or physical properties of the measuring sample at that time point.

With reference to FIG. 1A, an example of a coagulation waveform obtained by the method of the present embodiment will be described. In the coagulation waveform shown in FIG. 1A, a point a is the start point of measurement, a point b is the point of fibrin deposition (start point of coagulation), and a point c is the end point of coagulation. In a general method for measuring a coagulation time, the time until deposition of fibrin is regarded as the coagulation time. In FIG. 1A, the time between a-b shows the coagulation time. Since the coagulation proceeds by the action of the reagent for measuring a coagulation time, the transmittance of the measuring sample decreases as shown by a-c in FIG. 1A. However, the measuring sample contains the activating agent for fibrinolytic system, so that the fibrinolysis reaction starts when fibrin clots are formed. With reference to FIG. 1A, a point d is the start point of fibrinolysis, a point e is the point reaching the maximum rate after the initiation of fibrinolysis, a point f is the end point of fibrinolysis, and a point g is the end point of measurement. As shown by d-f in FIG. 1A, fibrin clots are decomposed by the fibrinolysis reaction, and thus the transmittance of the measuring sample increases again.

Figure 1B:
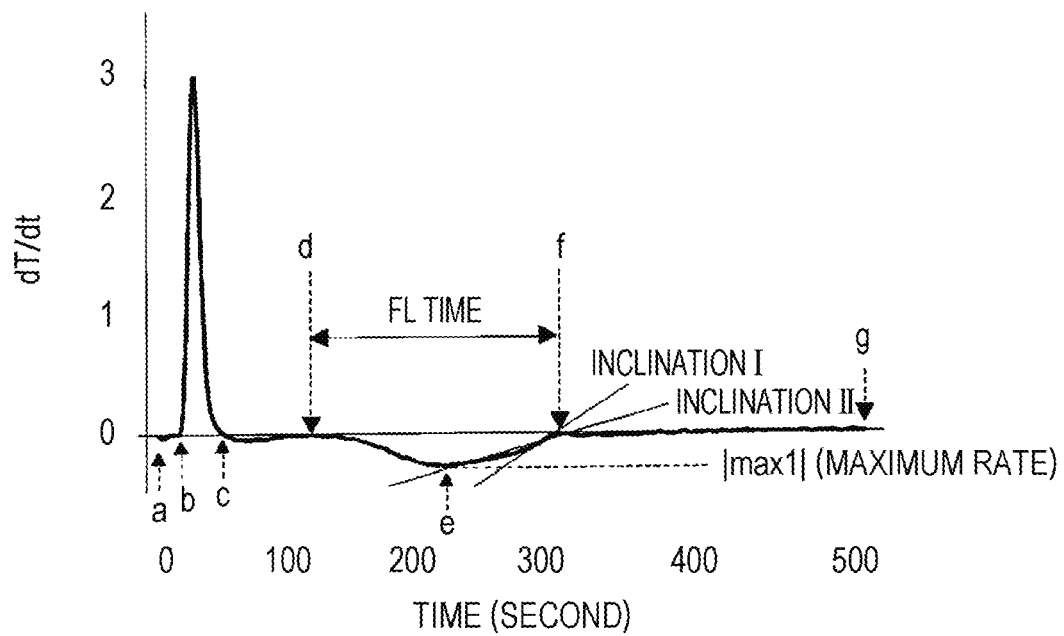
FIG. 1B is an example of a rate waveform obtained by primary differentiation of the coagulation waveform of FIG. 1A.

In the present embodiment, it is preferred that at least one parameter regarding differentiation of the coagulation waveform be acquired based on the coagulation waveform. This parameter should be a value regarding the rate waveform of coagulation and fibrinolysis obtained by primary differentiation of the coagulation waveform (hereinafter referred to as "rate waveform"). With reference to FIG. 1B, the rate waveform will be described. A waveform of coagulation and fibrinolysis rate shown in FIG. 1B is obtained by primary differentiation of the coagulation waveform shown in FIG. 1A. In FIG. 1B, the waveform is displayed in such a manner that the coagulation rate (the rate between a-c) is a positive value. Alternatively, the waveform may be displayed in such a manner that the coagulation rate is a negative value. More specifically, a waveform may be acquired in which positive and negative of the ordinate in FIG. 1B are reversed. The points a to g in FIG. 1B correspond to the points a to g in FIG. 1A, respectively. In FIG. 1B, the point c, which is the end point of coagulation, is a point where the increased rate becomes 0. The point d, which is the start point of fibrinolysis, is a point where the rate is closest to 0 after completion of coagulation. The point e is, in common with FIG. 1A, a point where the rate after the initiation of fibrinolysis (the rate between d-f) is the maximum value. The rate after the initiation of fibrinolysis will be hereinafter referred to as "fibrinolysis rate". The point f, which is the end point of fibrinolysis, is a point where the fibrinolysis rate is closest to 0 after reaching the maximum.

Figure 2:
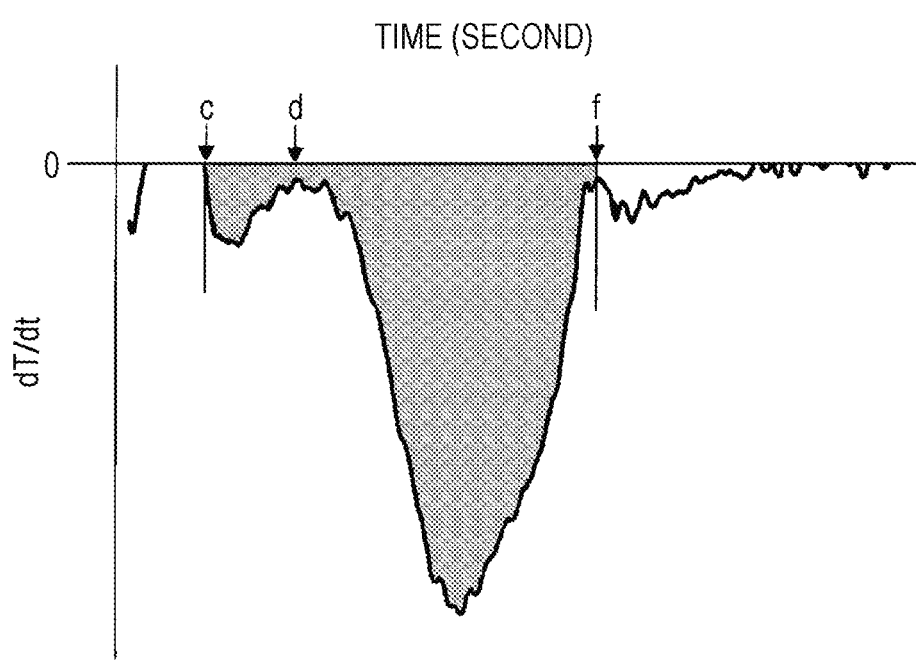
FIG. 2 is a view showing an example of an area as a parameter regarding differentiation of a coagulation waveform.

Examples of the parameter regarding differentiation of the coagulation waveform include, but are not limited to, |max 1|, inclination I, inclination II, FL time, area, and time reaching the maximum fibrinolysis rate. Typical parameters in the present embodiment are described. The "|max 1|" is, in the rate waveform, an absolute value of the maximum rate value after the initiation of fibrinolysis. Hereinafter |max 1| will be also referred to as "maximum fibrinolysis rate" or "maximum rate". The "inclination I" is, in the rate waveform, an absolute value of the inclination value of a straight line connecting the end point of fibrinolysis and a predetermined point on the curve of the waveform, the straight line having a correlation coefficient ($R^2$) of 0.95 or more with reference to the curve of the waveform. The "inclination II" is, in the rate waveform, an absolute value of the inclination value of a straight line connecting the point reaching the maximum rate after the initiation of fibrinolysis and a predetermined point on the curve of the waveform, the straight line having a correlation coefficient ($R^2$) of 0.95 or more with reference to the curve of the waveform. The "FL time" is, in the rate waveform, a time value from the initiation of fibrinolysis to the end point thereof. FIG. 1B shows examples of the |max 1|, straight line having inclination I, straight line having inclination II, and FL time. The "area" is, in the rate waveform, an area value of a region surrounded by the curve of the waveform and the abscissa (axis representing time) between the end point of coagulation and the end point of fibrinolysis. FIG. 2 shows an example of the area. With reference to FIG. 2, the area value as a parameter is the area value of the region shown in gray. In FIG. 2, the portion where the ordinate (rate) is negative is enlarged. "The time reaching the maximum fibrinolysis rate" is, in the rate waveform, a time from the initiation of measurement through the time reaching the maximum rate value after the initiation of fibrinolysis. With reference to FIG. 1B, the time reaching the maximum fibrinolysis rate is a time between a-e.

In the present embodiment, one or two or more parameters may be acquired. The parameter regarding differentiation of the coagulation waveform may be a value obtained by combining two or more parameters, and examples thereof include sum, difference, product, and ratio of at least two values selected from |max 1|, inclination I, inclination II, FL time, area, and time reaching the maximum fibrinolysis rate.

In the present method, information regarding the fibrinolytic capacity of the blood specimen is acquired based on the coagulation waveform thus acquired. When the parameter regarding differentiation of the coagulation waveform has been acquired based on the coagulation waveform, it is preferred that information regarding the fibrinolytic capacity of the blood specimen be acquired based on the parameter value thus acquired. Examples of the information regarding the fibrinolytic capacity of the blood specimen include information regarding the presence or absence of abnormality in the fibrinolytic system, information about whether the fibrinolytic capacity is promoted or not, and information about whether the fibrinolytic capacity is lowered or not.

The information regarding the fibrinolytic capacity of the blood specimen is preferably acquired based on the result of comparison between the parameter values acquired and normal ranges corresponding to these parameters. For example, when |max 1| has been acquired, a |max 1| value is compared with a first normal range. When the inclination I has been acquired, an inclination I value is compared with a second normal range. When the inclination II has been acquired, an inclination II value is compared with a third normal range. When the FL time has been acquired, an FL time value is compared with a fourth normal range. When the area has been acquired, an area value is compared with a fifth normal range. When the time reaching the maximum fibrinolysis rate has been acquired, a time value is compared with a sixth normal range. As a result of the comparison, when at least one of the parameter values regarding differentiation of the acquired coagulation waveform is out of the normal range corresponding to the parameter, information indicating abnormality in the fibrinolytic system can be acquired as the information regarding the fibrinolytic capacity of the blood specimen.

In the present description, when the parameter value is outside the normal range, the parameter value is more than or less than the normal range. When the parameter value is more than the normal range, the parameter value is more than the upper limit of the normal range. When the parameter value is less than the normal range, the parameter value is less than the lower limit of the normal range.

The normal range is not particularly limited, and examples thereof include ranges of values of the respective parameters that can be shown by a blood specimen of a healthy subject. This normal range can be set by, for example, preparing measuring samples from blood plasma obtained from a plurality of healthy subjects, obtaining various parameter values regarding differentiation of the coagulation waveform from these measuring samples, and accumulating the data. When there is few variation in the values that can be shown by the blood specimen of a healthy subject, the normal range may be replaced with a predetermined cutoff value in the above-described comparison. The cutoff value may be, for example, a parameter value that is acquired from the parameter values of a blood specimen of a healthy subject and that of a patient having an abnormality in the fibrinolytic system and that allows clear distinction between the healthy subject and the patient.

In conventional examination of the fibrinolytic system, the presence or absence of abnormality in the fibrinolytic system can be found, but the cause of the abnormality cannot be identified. Contrary to this, in the method of the present embodiment, when information that the fibrinolytic system in a blood specimen has an abnormality is acquired, information about which of the deficiency in α2AP, PAI-1, or plasminogen is the cause of the abnormality can be further acquired. Specifically, the cause of the abnormality in the fibrinolytic system can be presumed according to which parameter value is more than or less than the normal range corresponding to the parameter.

For example, when any one of the |max 1|, inclination I, inclination II, FL time, area, and time reaching the maximum fibrinolysis rate values is acquired as the parameter value regarding differentiation of the coagulation waveform, information about the cause of abnormality in the fibrinolytic system can be acquired as follows.

On comparison between the |max 1| value and the first normal range, when the |max 1| value is more than the first normal range, the information that the cause of abnormality in the fibrinolytic system is α2AP deficiency can be acquired. On the other hand, when the |max 1| value is less than the first normal range, the information that the cause of abnormality in the fibrinolytic system is plasminogen deficiency can be acquired.

On comparison between the inclination I value and the second normal range, when the inclination I value is more than the second normal range, the information that the cause of abnormality in the fibrinolytic system is α2AP deficiency can be acquired. On the other hand, when the inclination I value is less than the second normal range, the information that the cause of abnormality in the fibrinolytic system is PAI-1 deficiency can be acquired.

On comparison between the inclination II value and the third normal range, when the inclination II value is more than the third normal range, the information that the cause of abnormality in the fibrinolytic system is α2AP deficiency can be acquired. On the other hand, when the inclination II value is less than the third normal range, the information that the cause of abnormality in the fibrinolytic system is PAI-1 or plasminogen deficiency can be acquired.

On comparison between the FL time value and the fourth normal range, when the FL time value is more than the fourth normal range, the information that the cause of abnormality in the fibrinolytic system is PAI-1 deficiency can be acquired. On the other hand, when the FL time value is less than the fourth normal range, the information that the cause of abnormality in the fibrinolytic system is α2AP deficiency can be acquired.

On comparison between the area value and the fifth normal range, when the area value is more than the fifth normal range, the information that the cause of abnormality in the fibrinolytic system of the blood specimen is α2-AP or PAI-1 deficiency can be acquired.

On comparison between the time reaching the maximum fibrinolysis rate value and the sixth normal range, when the time value is more than the sixth normal range, the information that the cause of abnormality in the fibrinolytic system is PAI-1 or plasminogen deficiency can be acquired.

In the present embodiment, information that the blood specimen is a specimen suspected of having α2AP deficiency may be acquired. This information can be acquired as follows. First, as the parameter regarding differentiation of the coagulation waveform, at least one, preferably at least two or three, more preferably all of the |max 1|, inclination I, inclination II, and FL time values are acquired. Then, when the |max 1|value is acquired, the |max 1| value is compared with the first normal range; when the inclination I value is acquired, the inclination I value is compared with the second normal range; when the inclination II value is acquired, the inclination II value is compared with the third normal range; and when the FL time value is acquired, the FL time value is compared with the fourth normal range. As a result of the comparison, when at least one, preferably at least two, more preferably all of the |max 1|, inclination I, and inclination II values thus acquired are more than the normal range corresponding to each of the parameter values, and/or the FL time value is less than the fourth normal range, the information that the blood specimen is a specimen suspected of having α2AP deficiency is acquired.

In the present embodiment, information that the blood specimen is a specimen suspected of having PAI-1 deficiency may be acquired. This information can be acquired as follows. First, as the parameter regarding differentiation of the coagulation waveform, at least one, preferably all of the inclination I and FL time values are acquired. Then, when the inclination I value is acquired, the inclination I value is compared with the second normal range; and when the FL time value is acquired, the FL time value is compared with the fourth normal range. As a result of the comparison, when the inclination I value is less than the second normal range, and/or the FL time value is more than the fourth normal range, the information that the blood specimen is a specimen suspected of having PAI-1 deficiency is acquired.

In the present embodiment, information that the blood specimen is a specimen suspected of having plasminogen deficiency may be acquired. This information can be acquired as follows. First, as the parameter regarding differentiation of the coagulation waveform, the |max 1| and time reaching the maximum fibrinolysis rate values are acquired. Then, the |max 1| value is compared with the first normal range, and the time reaching the maximum fibrinolysis rate value is compared with the sixth normal range. As a result of the comparison, when the |max 1| value is less than the first normal range, and the time reaching the maximum fibrinolysis rate value is more than the sixth normal range, the information that the blood specimen is a specimen suspected of having plasminogen deficiency is acquired.

In the present embodiment, information that the blood specimen is a specimen suspected of having any of α2AP deficiency, PAI-1 deficiency, and plasminogen deficiency may be acquired. This information can be acquired as follows. First, as the parameter regarding differentiation of the coagulation waveform, the |max 1| and inclination I values are acquired. Next, the inclination I value is compared with the second normal range. As a result of the comparison, when the inclination I value is more than the second normal range, the information that the blood specimen is a specimen suspected of having α2AP deficiency can be acquired. When the inclination I value is less than the second normal range, the |max 1| value is compared with the first normal range. When the |max 1| value is less than the first normal range, the information that the blood specimen is a specimen suspected of having plasminogen deficiency can be acquired. On the other hand, when the |max 1| value is within or more than the first normal range, the information that the blood specimen is a specimen suspected of having PAI-1 deficiency can be acquired. The inclination II value may be used in place of the inclination I value.

[2. Reagent for Analyzing Blood Specimen]

Figure 6:
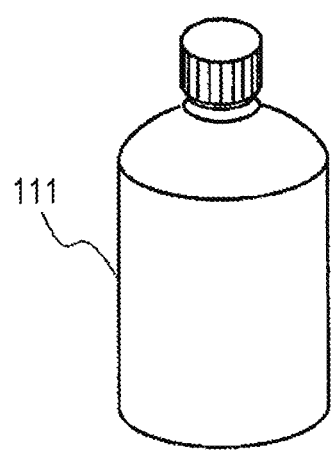
FIG. 6 is a view showing an example of an external appearance of a blood analytical reagent.

The scope of the present disclosure includes a reagent for analyzing a blood specimen (hereinafter may be referred to simply as "reagent"). A reagent according to the second aspect contains an activating agent for fibrinolytic system and a reagent for measuring a coagulation time. The reagent of the second aspect is preferably used for the method for analyzing a blood specimen. With reference to FIG. 6, a blood analytical reagent is accommodated in a first container 111. The details of the activating agent for fibrinolytic system and reagent for measuring a coagulation time are the same as those given for the above-described method for analyzing a blood specimen.

The form of the reagent may be a solid (powder, crystal, or granule, etc.) or a liquid, and is preferably a liquid. The solvent is not particularly limited as long as it will not hinder coagulation and fibrinolysis, and examples thereof include water, saline solution, and buffer.

The concentration of the activating agent for fibrinolytic system in the reagent is not particularly limited as long as the final concentration in a measuring sample can be adjusted within the range described in the above-described method for analyzing a blood specimen. When a measuring sample is prepared by a full automatic coagulation time measuring apparatus, the concentration of the activating agent for fibrinolytic system in the reagent may be determined in consideration of the reagent amount that can be sucked by the apparatus. For example, when t-PA is used as the activating agent for fibrinolytic system, the concentration of t-PA in the reagent is 0.1 µg/mL or more and 10 µg/mL or less, preferably 0.3 µg/mL or more and 5 µg/mL or less, and more preferably 0.5 µg/mL or more and 3 µg/mL or less.

The reagent of the second aspect may further contain an activating agent for coagulation system. The type and concentration of the activating agent for coagulation system can be determined as appropriate according to the type of the coagulation time to be measured. The details of the activating agent for coagulation system are the same as those given for the above-described method for analyzing a blood specimen.

The reagent of the second aspect may further contain a phospholipid. The concentration of the phospholipid in the reagent is not particularly limited as long as the final concentration in the measuring sample can be adjusted within the range described in the above-described method for analyzing a blood specimen. The details of the phospholipid are the same as those given for the above-described method for analyzing a blood specimen.

The reagent of the second aspect is substantially free from calcium ions. When the reagent for measuring a coagulation time is a reagent for measuring PT time, the reagent of the present embodiment may contain calcium ions in addition to an activating agent for fibrinolytic system and a tissue factor.

When the reagent for measuring a coagulation time is a reagent for measuring APTT time, the reagent of the second aspect may contain an activating agent for fibrinolytic system, a phospholipid, and an activating agent for coagulation system. In this case, the activating agent for coagulation system is preferably a substance activating a contact factor of the intrinsic coagulation pathway, and examples of the substance include ellagic acid, silica, kaolin, and celite.

The scope of the present disclosure also includes the use of an activating agent for fibrinolytic system and a reagent for measuring a coagulation time in the manufacture of a reagent for analyzing a blood specimen. More specifically, the present disclosure also relates to the use of an activating agent for fibrinolytic system and a reagent for measuring a coagulation time in the manufacture of a reagent for analyzing a blood specimen. For the manufacture of the reagent for analyzing a blood specimen, a phospholipid and/or an activating agent for coagulation system may be further used.

[3. Reagent Kit for Analyzing Blood Specimen]

Figure 7A:
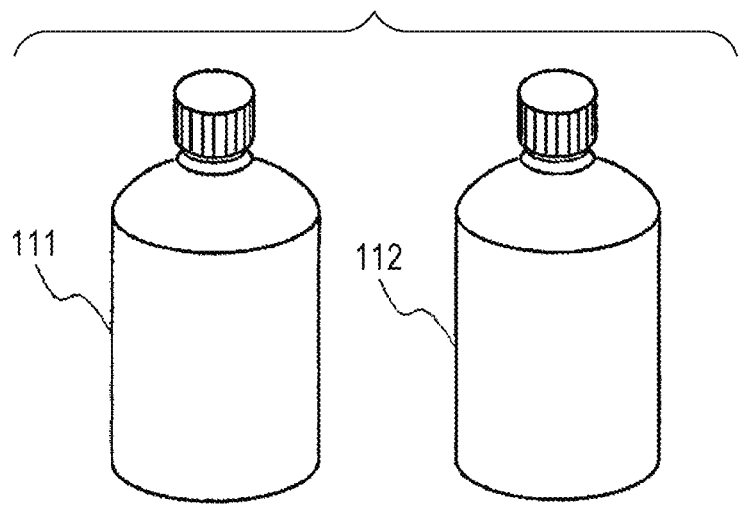
FIG. 7A is a view showing an example of an external appearance of a blood analytical reagent kit.

The scope of the present disclosure also includes a reagent kit for analyzing a blood specimen (hereinafter may be referred to simply as "reagent kit"). A reagent kit according to the third aspect includes first and second reagents. In the present embodiment, the first reagent contains an activating agent for coagulation system, and the second reagent contains calcium ions. The activating agent for fibrinolytic system should be contained in the first or second reagent. For example, the first reagent contains an activating agent for coagulation system, and the second reagent contains an activating agent for fibrinolytic system and calcium ions. Alternatively, the first reagent contains an activating agent for coagulation system and an activating agent for fibrinolytic system, and the second reagent contains calcium ions. The first reagent is substantially free from calcium ions. With reference to FIG. 7A, a first container 111 accommodates the first reagent, and a second container 112 accommodates the second reagent.

Figure 7B:
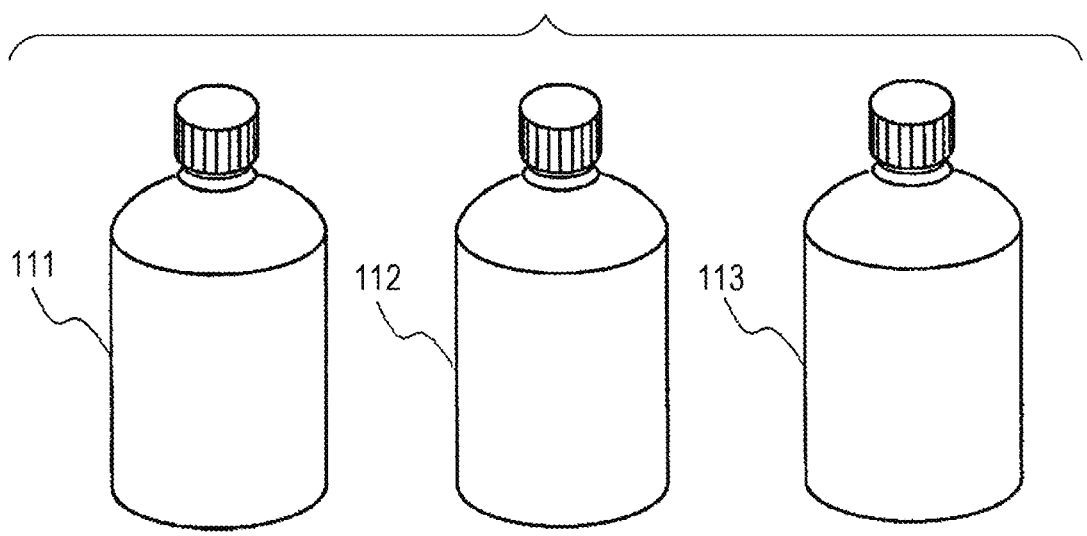
FIG. 7B is a view showing an example of an external appearance of a blood analytical reagent kit.

A reagent kit according to the fourth embodiment includes first, second, and third reagents. In the present embodiment, the first reagent contains an activating agent for coagulation system, the second reagent contains an activating agent for fibrinolytic system, and the third reagent contains calcium ions. The first and second reagents are substantially free from calcium ions. With reference to FIG. 7B, a first container 111 accommodates the first reagent, a second container 112 accommodates the second reagent, and a third container 113 accommodates the third reagent.

In the present embodiment, a container accommodating the above-described various reagents may be packed in a box and provided to the user. The box may also include a document attached to the reagent kit. The attached document preferably describes, for example, the constitution of the reagent kit and the protocol of the method for analyzing a blood specimen.

The reagent kits of the third and fourth embodiments are preferably used for the above-described method for analyzing a blood specimen. The details of the activating agent for fibrinolytic system, activating agent for coagulation system, and calcium ions are the same as those given for the above-described method for analyzing a blood specimen.

The form of the reagents contained in the reagent kits of the third and fourth embodiments may be a solid (for example, powder, crystal, granule, etc.) or a liquid, and is preferably a liquid. The details of the solvent are the same as those given for the above-described method for analyzing a blood specimen.

In the reagent kits of the third and fourth embodiments, the first reagent may further contain a phospholipid. The concentration of the phospholipid in the reagent is not particularly limited as long as the final concentration in the measuring sample can be adjusted within the range described in the above-described method for analyzing a blood specimen. The details of the phospholipid are the same as those given for the above-described method for analyzing a blood specimen.

When a blood specimen is analyzed based on the measurement principle of APTT, the reagent kit of the third aspect is preferably used which includes the first reagent containing an activating agent for coagulation system and a phospholipid, and the second reagent containing an activating agent for fibrinolytic system and calcium ions.

The scope of the present disclosure also includes the use of the above-described various reagents in the manufacture of a reagent kit for analyzing a blood specimen. More specifically, the present disclosure also relates to the use of the first and second reagents in the manufacture of a reagent kit for analyzing a blood specimen, the first reagent containing an activating agent for coagulation system, and the second reagent containing an activating agent for fibrinolytic system and calcium ions, or the first reagent containing an activating agent for coagulation system and an activating agent for fibrinolytic system, and the second reagent contains calcium ions.

The present disclosure also relates to the use of the first, second, and third reagents in the manufacture of a reagent kit for analyzing a blood specimen, the first reagent containing an activating agent for coagulation system, the second reagent containing an activating agent for fibrinolytic system, and the third reagent containing calcium ions.

[4. Blood Specimen Analyzer]

Figure 8:
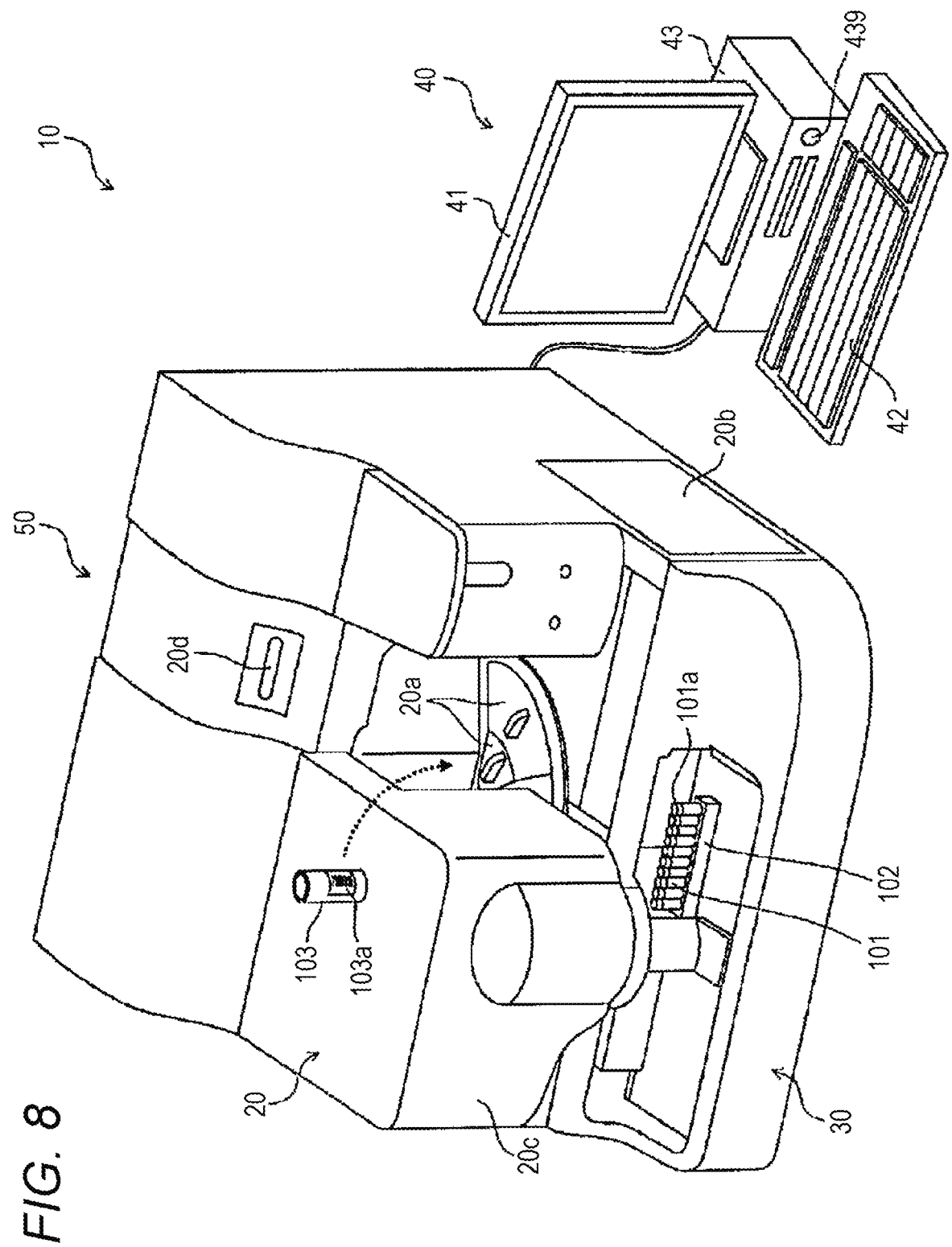
FIG. 8 is a perspective view showing a structure of an external appearance of a blood specimen analyzer.

An example of the blood specimen analyzer of the fifth embodiment is described below with reference to the drawings. However, the present embodiment will not be limited to this example alone. As shown in FIG. 8, a blood specimen analyzer 10 includes a measuring apparatus 50 for preparing and measuring a measuring sample, and a controller 40 for analyzing the measurement data acquired by the measuring apparatus 50, and giving directions to the measuring apparatus 50. The measuring apparatus 50 includes a measurement unit 20 for acquiring optical information from the measuring sample, and a specimen transfer unit 30 located ahead of the measurement unit 20.

The measurement unit 20 is equipped with caps 20a and 20b, a cover 20c, and a power button 20d. The user can open the cap 20a and replace reagent containers 103, which are placed on the reagent tables 11 and 12 (see FIG. 9), with new reagent containers 103, or newly add another reagent container 103. A bar code label 103a, which is printed with a bar code containing the type of the reagent to be accommodated and the reagent ID composed of the serial number given to the reagent, is attached to the reagent container 103.

Figure 9:
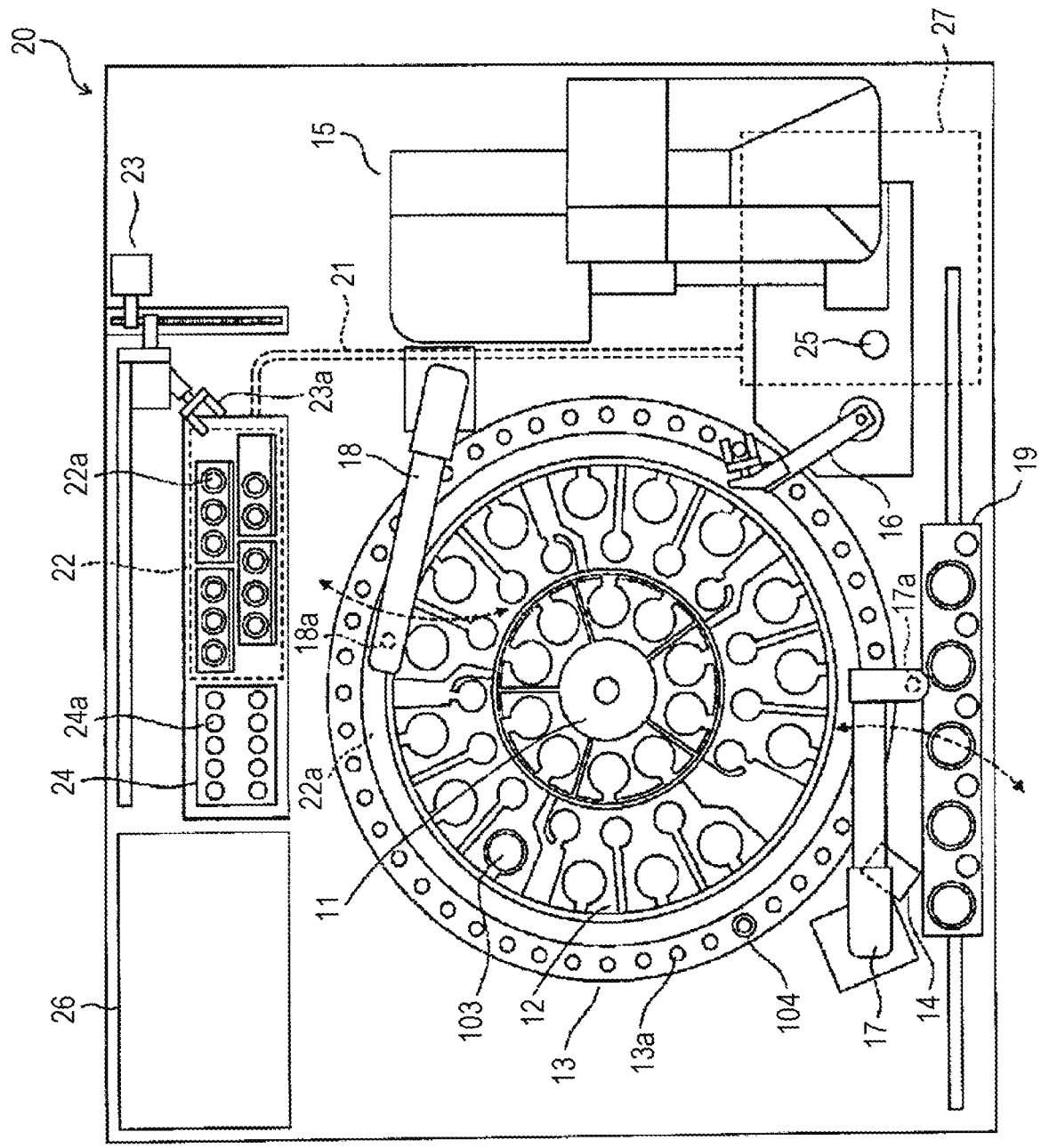
FIG. 9 is a top plan view of an inside of a measurement unit of a blood specimen analyzer.

The user can open the cap 20b and replace a lamp unit 27 (see FIG. 9). In addition, the user can open the cover 20c and replace a piercer 17a (see FIG. 9). The specimen transfer unit 30 transfers a specimen container 101 supported by a specimen lack 102 to the position to be sucked by a piercer 17a. The specimen container 101 is sealed with a rubber cap 101a.

When the blood specimen analyzer 10 is used, firstly, the user pushes the power button 20d of the measurement unit 20 for starting the measurement unit 20, and pushes a power source button 439 of the controller 40 to start the controller 40. Upon starting of the controller 40, a log-on screen is displayed on a display unit 41. The user enters the user name and password on the log-on screen to log on the controller 40, and starts the use of the blood specimen analyzer 10.

(Structure of Measuring Apparatus)

The structure of the measuring apparatus 50 is described below. The measurement unit 20 includes, as shown in FIG. 9, the reagent tables 11 and 12, a cuvette table 13, a bar code reader 14, a cuvette feeding unit 15, a catcher 16, a specimen dispensing arm 17, a reagent dispensing arm 18, an urgent specimen set unit 19, an optical fiber 21, a detection unit 22, a cuvette transfer unit 23, a warming unit 24, a waste vent 25, a fluid unit 26, and a lamp unit 27.

(Measurement Sample Preparation Unit)

Each of the reagent tables 11 and 12, and cuvette table 13 has an annular ring shape, and is rotatably composed. The reagent tables 11 and 12 correspond to reagent accommodation units, and the reagent containers 103 are placed thereon. The bar code of the reagent containers 103 placed on the reagent tables 11 and 12 is read by the bar code reader 14. The information read from the bar code (the type of the reagent, reagent ID) is inputted into the controller 40, and stored in a hard disk 434 (see FIG. 14).

In the analyzer of the present embodiment, the reagent containers 103 containing, for example, a reagent for measuring coagulation time, a solution containing an activating agent for fibrinolytic system, or a calcium solution are placed on the reagent table 11 and/or 12. Alternatively, the reagent containers 103 containing the above-described blood analytical reagent or reagent kit for blood analysis may be placed thereon. In addition, the reagent containers 103 containing normal blood plasma as a control specimen may be placed on the reagent tables 11 and/or 12.

Support 13a composed of a plurality of holes which can support cuvettes 104 is formed on the cuvette table 13. The new cuvette 104 put into the cuvette feeding unit 15 by the user is transferred successively by the cuvette feeding unit 15, and placed in the support 13a of the cuvette table 13 by the catcher 16.

Stepping motors are connected to each of the specimen dispensing arm 17 and reagent dispensing arm 18 so as to be vertically and rotatably movable. The tip of the specimen dispensing arm 17 has the piercer 17a whose tip is sharpened so as to pierce the cap 101a of the specimen container 101. The tip of the reagent dispensing arm 18 has a pipette 18a. The tip of the pipette 18a is flat, different from the piercer 17a. In addition, a liquid level detection sensor 213 of capacitance type (see FIG. 10) is connected to the pipette 18a.

Once the specimen container 101 is transferred to a predetermined position by the specimen transfer unit 30 (see FIG. 8), the piercer 17a is located immediately above the specimen container 101 by rotary moving of the specimen dispensing arm 17. In addition, the specimen dispensing arm 17 is moved vertically, the piercer 17a penetrates through the cap 101a of the specimen container 101, and the blood specimen accommodated in the specimen container 101 is sucked by the piercer 17a. When a blood specimen requiring urgent examination is mounted on the urgent specimen set unit 19, the piercer 17a sucks the blood specimen before the specimen fed from the measuring sample transfer unit 3. The blood specimen sucked by the piercer 17a is ejected into an empty cuvette 104 on the cuvette table 13.

The cuvette 104 into which the blood specimen has been ejected is transferred by a catcher 23a of the cuvette transfer unit 23 from the support 13a of the cuvette table 13 to supports 24a of the warming unit 24. The warming unit 24 warms the blood specimen accommodated in the cuvettes 104 mounted on the supports 24a to a predetermined temperature (for example, 36 to 38° C.) for a certain time. When warming of the blood specimen by the warming unit 24 is finished, the cuvettes 104 are held again by the catcher 23a. Then, the cuvettes 104 are located at predetermined positions with being held by the catcher 23a, and, in this state, the reagent sucked by the pipette 18a is ejected into the cuvettes 104.

When a reagent is dispensed by the pipette 18a, firstly, the reagent tables 11 and 12 are rotated, and the reagent container 103 accommodating the reagent corresponding to the measurement item is transferred to the position sucked by the pipette 18a. Then, based on the sensor for detecting the position of origin, the vertical position of the pipette 18a is located at the point of origin, and then the pipette 18a is lowered until the lower end of the pipette 18a touches the liquid level of the reagent, which is detected by the liquid level detection sensor 213. When the lower end of the pipette 18a touches the liquid level of the reagent, the pipette 18a is further lowered so as to suck a necessary amount of the reagent. Then, lowering of the pipette 18a is stopped, and the reagent is sucked by the pipette 18a. The reagent sucked by the pipette 18a is ejected into the cuvettes 104 held by the catcher 23a. Then, the blood specimen and reagent in the cuvettes 104 are stirred by vibration function of the catcher 23a. As a result of this, preparation of the measuring sample is achieved. Thereafter, the cuvettes 104 accommodating the measuring sample are transferred by the catcher 23a to a support 22a of the detection unit 22.

(Information Acquisition Unit)

Figure 11:
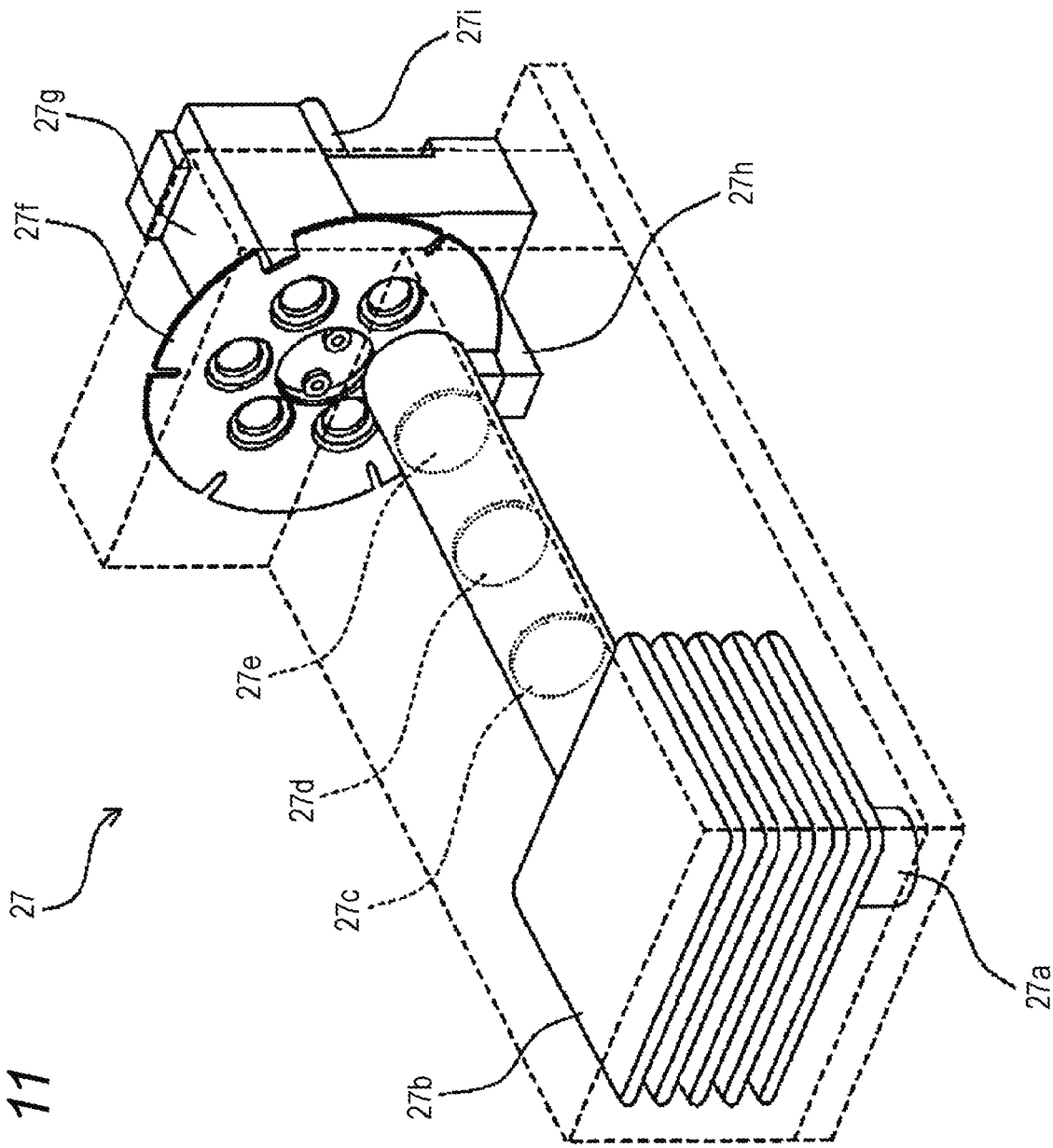
FIG. 11 shows a structure of a lamp unit included in a measuring apparatus.

The lamp unit 27 supplies light having different types of wavelength used for the detection of optical signals by the detection unit 22. With reference to FIG. 11, an example of the structure of the lamp unit 27 is described. The lamp unit 27 corresponds to a light source, and includes a halogen lamp 27a, a lamp case 27b, converging lenses 27c to 27e, a filter unit 27f in a disk shape, a motor 27g, a sensor 27h of optical transmission type, and an optical fiber coupler 27i.

With reference to FIG. 9, the light from the lamp unit 27 is supplied to the detection unit 22 through the optical fiber 21. The detection unit 22 has a plurality of hole supports 22a, and the cuvette 104 can be inserted into each of the supports 22a. Each support 22a is equipped with the end of the optical fiber 21, which allows irradiation of the cuvettes 104 supported by support 22a with the light from the optical fiber 21. The detection unit 22 irradiates the cuvettes 104 with the light supplied from the lamp unit 27 through the optical fiber 21, and detects the quantity of light passing through the cuvettes 104 (or scattered light from the cuvettes 104).

Figure 12A:
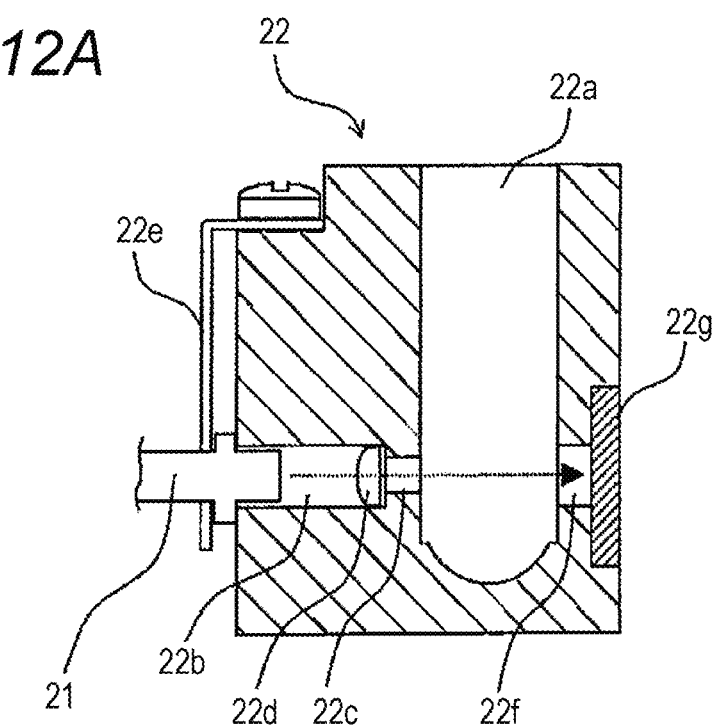
FIG. 12A is a view showing a structure of a detection unit included in the measuring apparatus.

With reference to FIGS. 12A to D, an example of the structure of the plurality of supports 22a provided in the detection unit 22 is shown, and other supports 22a also have a similar structure. With reference to FIG. 12A, a circular hole 22b, through which the tip of the optical fiber 21 is inserted, is formed in the detection unit 22. A circular communication hole 22c for communicating the hole 22b with the support 22a is formed in the detection unit 22. The diameter of the hole 22b is larger than that of the communication hole 22c. A lens 22d for gathering light from the optical fiber 21 is arranged at the end of the hole 22b. A hole 22f is formed in the inner wall of the support 22a at the position opposed to the communication hole 22c. A light detector 22g is arranged in the deep portion of the hole 22f. The light detector 22g corresponds to a photosensor, and outputs electric signals according to the quantity of received light. The light after passing through the lens 22d is gathered by the light receiving surface of the light detector 22g through the communication hole 22c, support 22a, and hole 22f. The optical fiber 21 is locked by a leaf spring e with its end inserted into the hole 22e.

Figure 12B:
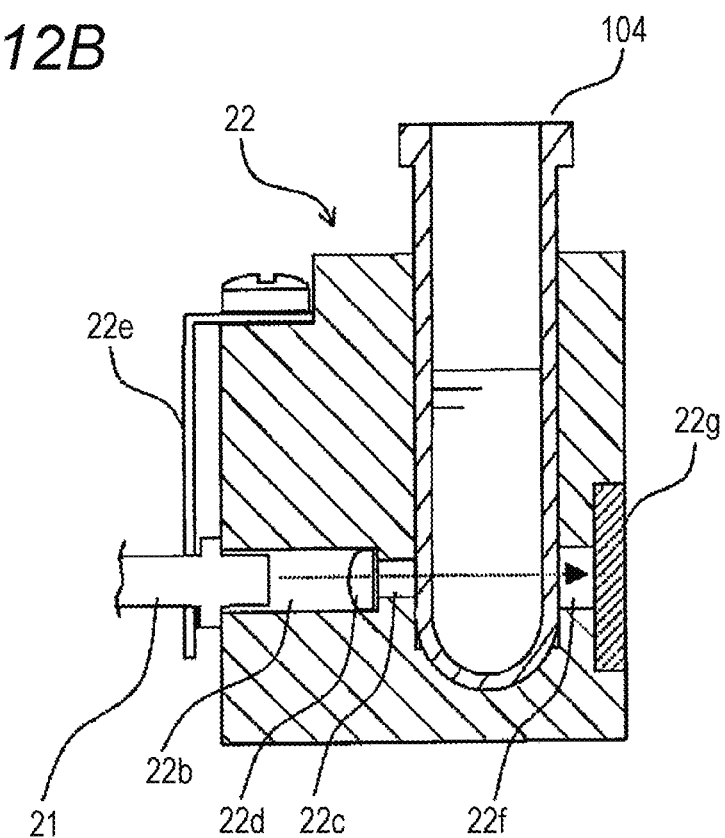
FIG. 12B is a view showing the structure of the detection unit included in the measuring apparatus.

With reference to FIG. 12B, when the cuvettes 104 are supported by the support 22a, the light gathered by the lens 22d passes through the cuvettes 104 and the sample accommodated in the cuvettes 104, and enters into the light detector 22g. When blood coagulation reaction proceeds in the sample, turbidity of the sample increases. Along with this, the quantity of light passing through the sample (the quantity of transmitted light) decreases, and the level of the detection signal of the light detector 22g also decreases.

Figure 12C:
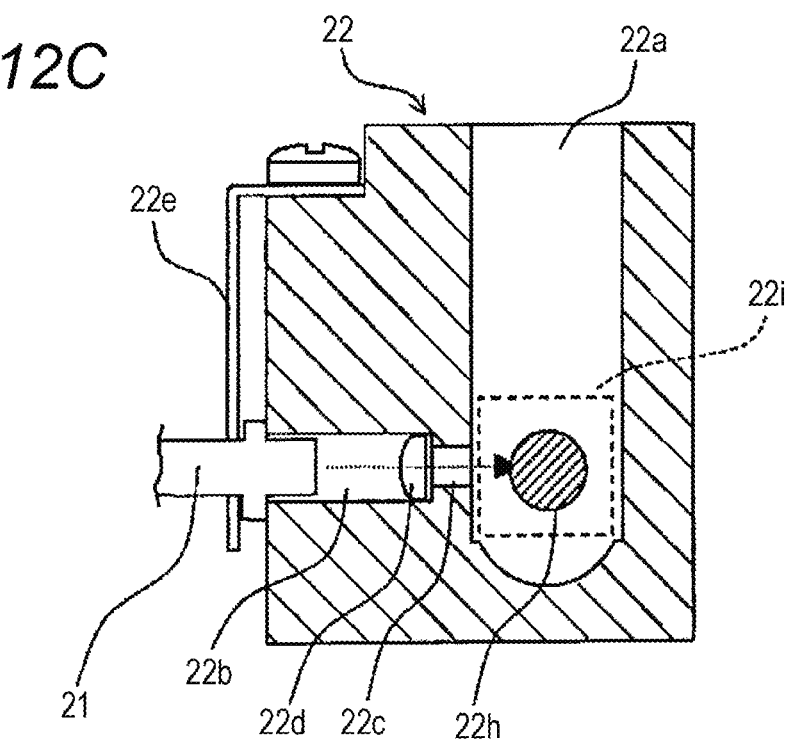
FIG. 12C is a view showing the structure of the detection unit included in the measuring apparatus.
Figure 12D:
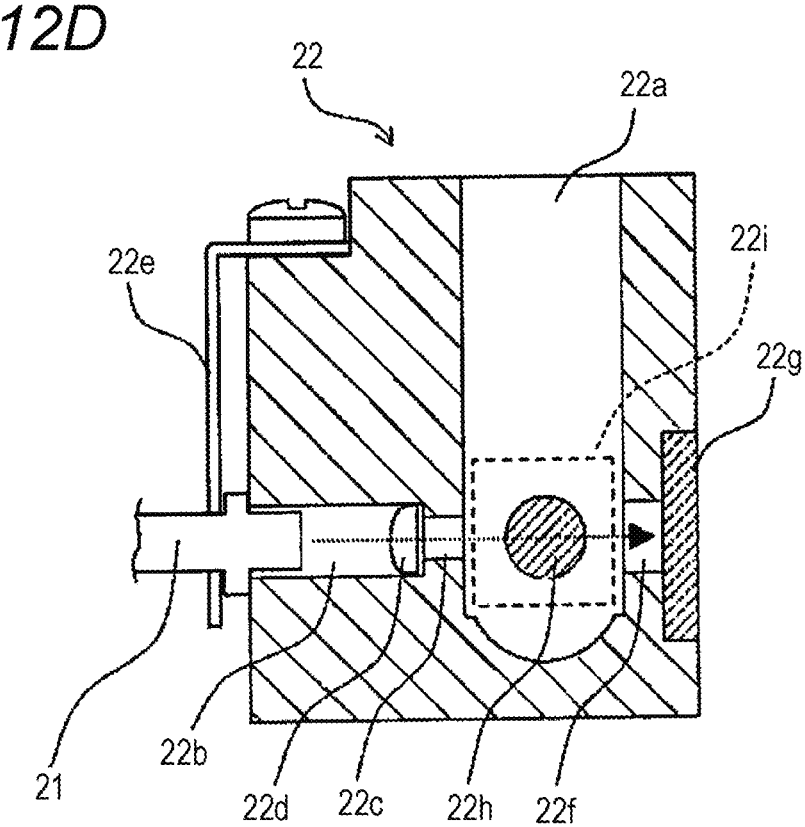
FIG. 12D is a view showing the structure of the detection unit included in the measuring apparatus.

With reference to FIG. 12C, the structure of the detection unit 22 using scattered light is described. The hole 22h is formed in the inside surface of the support 22a at the same height as the communication hole 22c. A light detector 22i is arranged at the deep portion of the hole 22h. When the cuvettes 104 are inserted into the support 22a, and light is emitted from the optical fiber 21, the light scattered by the measuring sample in the cuvettes 104 is applied to the light detector 22i through the hole 22h. In this example, the detection signal from the light detector 22i shows the intensity of light scattered by the measuring sample. As shown in FIG. 12D, both of the transmitted light passing through the measuring sample and the scattered light scattered by the measuring sample may be detected.

As described above, the detection unit 22 applies the light supplied from the lamp unit 27 to the cuvettes 104, and acquires optical information from the measuring sample. The acquired optical information is sent to the controller 40. The controller 40 carries out analysis based on the optical information, and displays the analysis result on the display unit 41.

After completion of measurement, unnecessary cuvettes 104 are transferred by the cuvette table 13, and discarded by the catcher 16 into the waste vent 25. At the time of the measurement operation, the piercer 17a and pipette 18a are washed as needed by a liquid such as a cleaning liquid supplied from the fluid unit 26.

Figure 10:
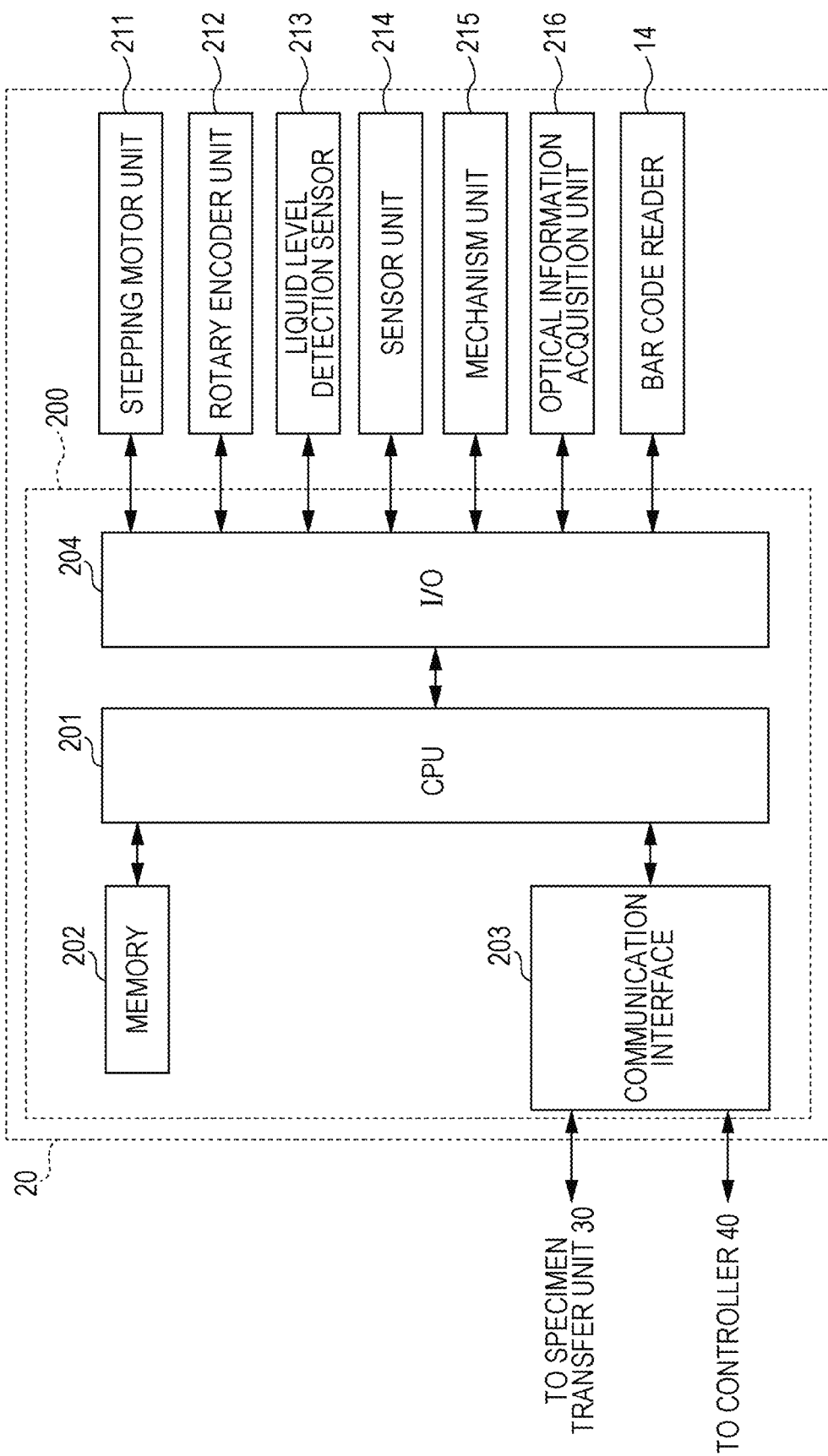
FIG. 10 is a view showing a structure of the measurement unit of the blood specimen analyzer.

The hardware structure of the measuring apparatus is described below. As shown in FIG. 10, the measurement unit 20 includes a control unit 200, a stepping motor unit 211, a rotary encoder unit 212, the liquid level detection sensor 213, a sensor unit 214, a mechanism unit 215, an optical information acquisition unit 216, and a bar code reader 14.

With reference to FIG. 10, the control unit 200 includes a CPU 201, a memory 202, a communication interface 203, and an I/O interface 204. The CPU 201 carries out the computer program stored in the memory 202. The memory 202 is composed of ROM, RAM, a hard disk, and others. The CPU 201 drives the specimen transfer unit 30 through the communication interface 203, and transmits and receives the instruction signal and data to and from the controller 40. The CPU 201 controls the units of the measurement unit 20 through the I/O interface 204, and receives the signals outputted from each unit.

The stepping motor unit 211 includes a stepping motor for driving the reagent tables 11 and 12, cuvette table 13, catcher 16, specimen dispensing arm 17, reagent dispensing arm 18, and cuvette transfer unit 23. A rotary encoder unit 212 includes a rotary encoder which outputs pulse signals according to the rotation displacement amounts of the stepping motors included in the stepping motor unit 211.

The liquid level detection sensor 213 is connected to the pipette 18a arranged at the tip of the reagent dispensing arm 18, and detects the touch of the lower end of the pipette 18a with the liquid level of the reagent. The sensor unit 214 includes a sensor for detecting that the vertical position of the pipette 18a is located at the origin, and a sensor for detecting that the power button 20d is pushed. The mechanism unit 215 includes a mechanism for driving the cuvette feeding unit 15, urgent specimen set unit 19, warming unit 24, and fluid unit 26, and an air pressure source for supplying pressure to the piercer 17a and pipette 18a so as to allow dispensing operation by the piercer 17a and pipette 18a. The optical information acquisition unit 216 includes, with reference to FIG. 9, at least, the lamp unit 27, optical fiber 21, and detection unit 22.

(Control Unit)

The structure of the controller 40 (control unit) is described below. As shown in FIG. 8, the controller 40 is composed of a display unit 41, an input unit 42, and a computer body 43. When the user inputs an instruction to start the measurement of a blood specimen through the input unit 42, the controller 40 transmits the instruction to start measurement to the measurement unit 20, and starts measurement. The controller 40 receives optical information from the measurement unit 20. Then, the processor of the controller 40 calculates the parameters regarding differentiation of the coagulation waveform based on the optical information. The processor of the controller 40 may calculate the coagulation time based on the optical information. In addition, the processor of the controller 40 carries out the computer program for analyzing the blood specimen. Accordingly, the controller 40 also works as a computer system for analyzing the blood specimen.

Figure 13:
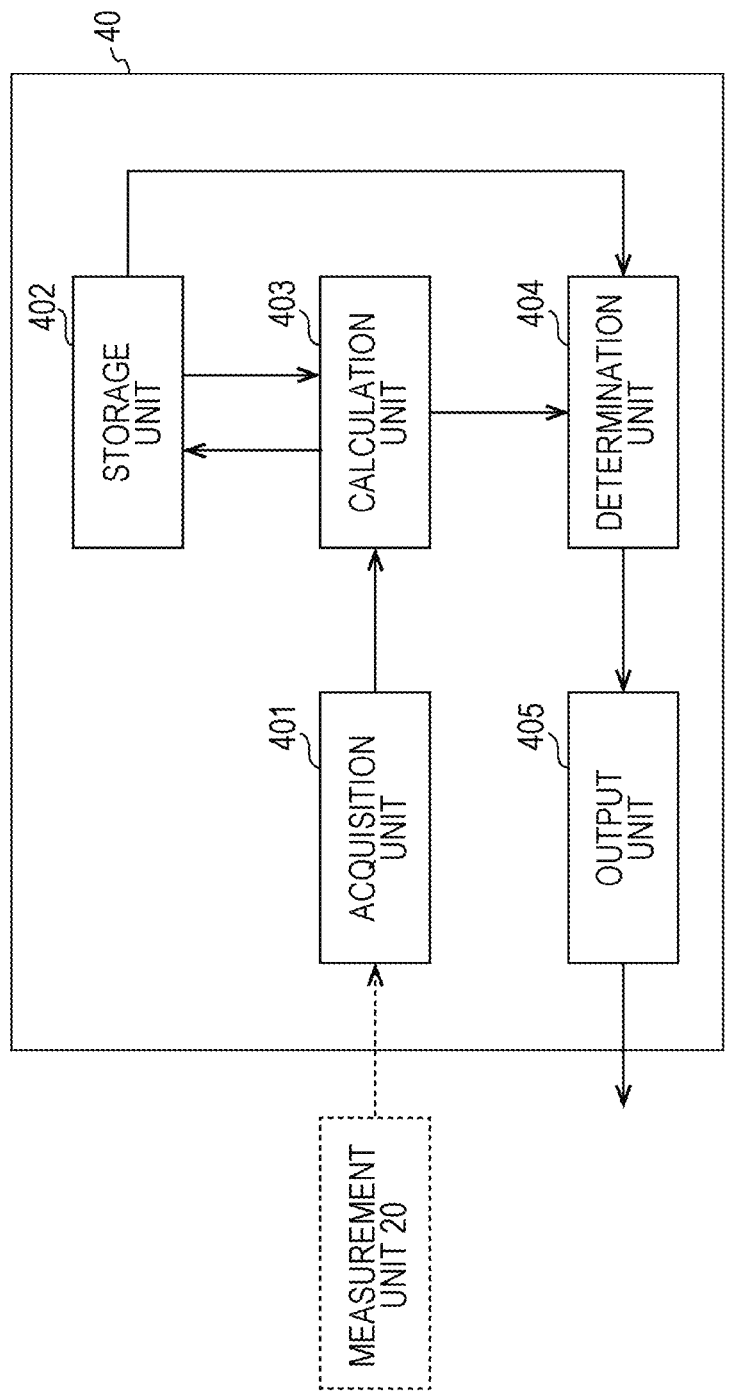
FIG. 13 is a view showing a function structure of a controller of a blood specimen analyzer.

As shown in FIG. 13, regarding the function structure of the controller 40, the controller 40 includes an acquisition unit 401, a memory unit 402, a calculation unit 403, a determination unit 404, and an output unit 405. The acquisition unit 401 is connected to the measurement unit 20 through a network so as to allow communication. The output unit 404 is connected to the display unit 41 so as to allow communication.

The acquisition unit 401 acquires the optical information transmitted from the measurement unit 20. The memory unit 402 stores the formula for calculating various parameter values regarding differentiation of the coagulation waveform, and normal ranges or predetermined cutoff values corresponding these parameters. The memory unit 402 may store the formula for calculating the coagulation time. The calculation unit 403 calculates various parameter values according to the formula stored in the memory unit 402 using the information acquired by the acquisition unit 401. The determination unit 404 determines whether the parameter values calculated by the calculation unit 403 are out of the normal ranges corresponding to these parameters stored in the memory unit 402. The output unit 405 outputs the parameter values calculated by the calculation unit 403 as the reference information about the blood specimen.

Figure 14:
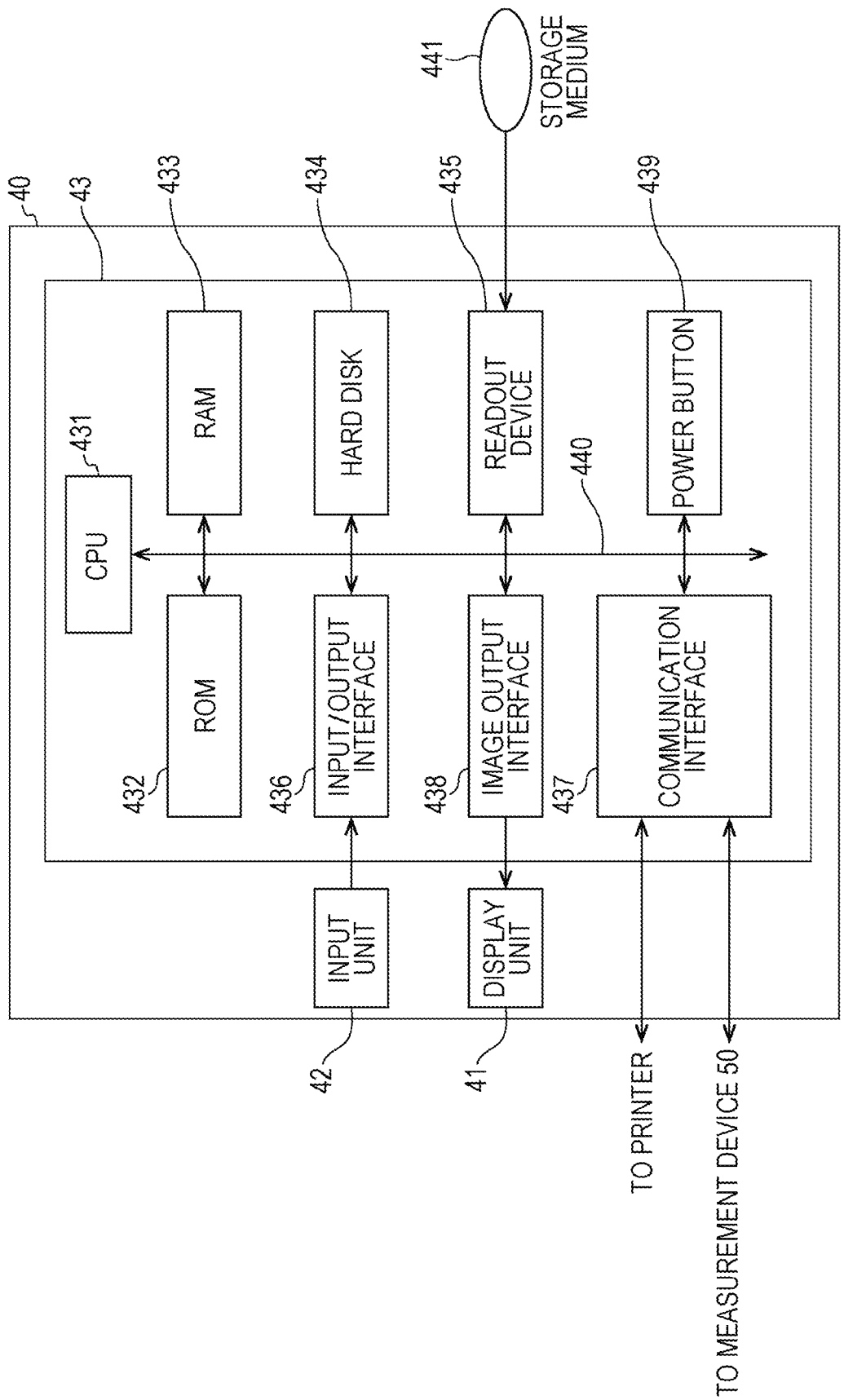
FIG. 14 is a view showing a hard ware structure of the controller of the blood specimen analyzer.

As shown in FIG. 14, the computer body 43 of the controller 40 includes a CPU 431, a ROM 432, a RAM 433, a hard disk 434, a readout device 435, an input/output interface 436, a communication interface 437, an image output interface 438, and a power source button 439. The CPU 431, ROM 432, RAM 433, hard disk 434, readout device 435, input/output interface 436, communication interface 437, image output interface 438, and power source button 439 are connected by a bus 440 so as to allow communication.

The CPU 431 carries out the computer programs stored in the ROM 432 and that loaded in RAM 433. The above-described function blocks are achieved by execution of the application program by the CPU 431. As a result of this, the computer system functions as a terminal of the blood specimen analyzer.

The ROM 432 is composed of a mask ROM, a PROM, an EPROM, an EEPROM, and others. The ROM 432 stores the computer program to be carried out by the CPU 431 and the data used for this.

The RAM 433 is composed of an SRAM, a DRAM, and others. The RAM 433 is used for readout of the computer programs stored in the ROM 432 and hard disk 434. The RAM 433 is also used as a work area of the CPU 431 when these computer programs are executed.

The hard disk 434 is loaded with an operating system, computer programs such as an application program for execution by the CPU 431 (computer program for analyzing the blood specimen), data used for execution of the computer programs, and the configuration content of the controller 40.

The readout device 435 is composed of a flexible disk drive, a CD-ROM drive, a DVD ROM drive, and others. The readout device 435 can read out the computer program or data stored on a portable storage medium 441 such as a CD or DVD.

The input/output interface 436 is composed of, for example, a serial interface including a USB, an IEEE1394, and an RS-232C, a parallel interface including an SCSI, an IDE, and an IEEE1284, and an analog interface including a D/A converter and an A/D converter. The input/output interface 436 is connected to an input unit 42 including a keyboard and a mouse. The user inputs an instruction through the input unit 42, and the input/output interface 436 receives the signal inputted through the input unit 42.

The communication interface 437 is, for example, an Ethernet (registered trademark) interface. The controller 40 can transmit print data to a printer through the communication interface 437. The communication interface 437 is connected to the measurement unit 20, and the CPU 431 transmits and receives the instruction signal and data to and from the measurement unit 20 through the communication interface 437.

The image output interface 438 is connected to the display unit 41 which is composed of an LCD, a CRT, and others. The image output interface 438 outputs image signals according to the image data to the display unit 41, and the display unit 41 displays images based on the image signals outputted from the image output interface 438.

With reference to FIG. 10, during the measurement operation, the CPU 201 of the measurement unit 20 temporarily stores the digitized data (optical information) of the detection signals outputted from the detection unit 22 (see FIG. 9) in the memory 202. The memory region of the memory 202 is divided into areas for each support 22*a*. In each area, the data (optical information) acquired when the cuvettes 104 supported by the corresponding support 22*a* are irradiated with light having a predetermined wavelength is stored one by one. In this manner, the data is stored in the memory 202 one by one for a predetermined measurement time. When the measurement time has elapsed, the CPU 201 stops storing the data in the memory 202, and transmits the stored data to the controller 40 through the communication interface 203. The controller 40 processes the received data for analysis, and displays the analysis result on the display unit 41.

(Modification of Information Acquisition Unit)

The coagulation waveform may be measured based on the physical information such as the change in viscosity caused by blood coagulation and fibrinolysis. When the coagulation waveform is measured based on the change in viscosity, the detection unit 22 includes a high frequency transmission coil, a high frequency receiving coil, a cuvette mounting unit for mounting the cuvettes containing steel balls placed between the high frequency transmission coil and high frequency receiving coil, and electromagnets installed at both ends of the cuvette mounting unit. The magnetic force generated by the electromagnets causes lateral amplitude motion of the steel balls in the cuvettes. This amplitude motion decreases with the increase in the viscosity. Once the coagulation of the measuring sample starts, the increase of the measuring sample increases, so that the amplitude of the steel balls decreases. Accordingly, the detection unit 22 detects the change in the amplitude when the high frequency transmitted by the high frequency transmission coil is received by the high frequency receiving coil. The controller 40 calculates the coagulation time based on the change in the detected amplitude.

(Processing Procedure of Blood Specimen Analyzer)

Figure 15:
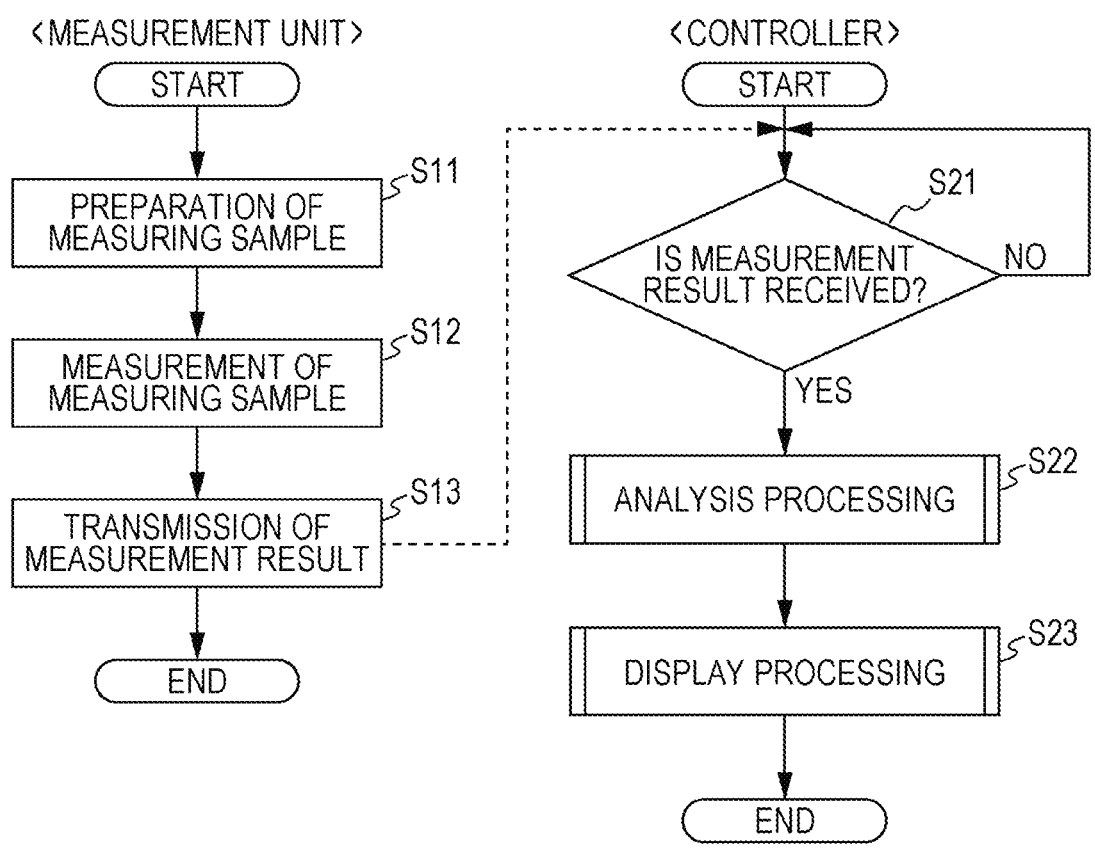
FIG. 15 is a flow chart showing processing of measuring a blood specimen by a blood specimen analyzer.

The processing in the measurement unit 20 is mainly carried out under control by the CPU 201 of the measurement unit 20, and processing in the controller 40 is mainly carried out under control by the CPU 431 of the controller 40. Once the measurement start instruction inputted by the user is received from the controller 40, the measurement unit 20 initiates measurement processing. With reference to FIG. 15, when the measurement processing is initiated, the measurement unit 20 sucks a predetermined amount of the blood specimen from the specimen container 101 which has been transferred by the specimen transfer unit, and dispenses the blood specimen into the empty cuvettes 104 on the cuvette table 13. When normal blood plasma is also measured as a control specimen, the measurement unit 20 sucks a predetermined amount of the normal blood plasma from the reagent container 103 which contains normal blood plasma and is accommodated in the reagent accommodation unit, and dispenses it into the empty cuvettes 104. The measurement unit 20 transfers the cuvettes 104 containing the dispensed specimen to the warming unit 24, and warms the blood plasma in the cuvettes 104 to a predetermined temperature (for example, 37° C.). Thereafter, the measurement unit 20 adds the reagent for measuring coagulation time, activating agent for fibrinolytic system, and calcium solution to the cuvettes 104, thereby preparing measuring samples (step S11).

The measurement unit 20 transfers the cuvettes 104 containing various reagents to the detection unit 22, and irradiates the cuvettes 104 with light for measuring the measuring sample (step S12). The measurement unit 20 initiates measuring of the time from the point of addition of the calcium solution to the cuvettes 104. In this measurement, the data based on light having a wavelength of 660 nm (quantity of scattered light or transmitted light) is stored in the memory 202 sequentially during the measurement time. At this time, the data is sorted in the memory 202 with being associated with the elapsed time from the point of addition of the calcium solution. After elapse of the measurement time, the measurement unit 20 aborts the measurement, and transmits the measurement result (data) stored in the memory 202 to the controller 40 (step S13). Once the controller 40 receives the measurement result (data) from the measurement unit 20 (step S21: YES), the controller 40 carries out analysis processing on the received measurement result (step S22). More specifically, the controller 40 calculates, regarding the measuring sample, parameters regarding differentiation of the coagulation waveform from the coagulation waveform. The controller 40 may also calculate the coagulation time and coagulation waveform of the measuring sample. After the analysis processing, the controller 40 carries out display processing on the analysis result (step S23).

(Processing Procedure of Acquisition of Information Regarding Fibrinolytic Capacity of Blood Specimen)

Figure 16:
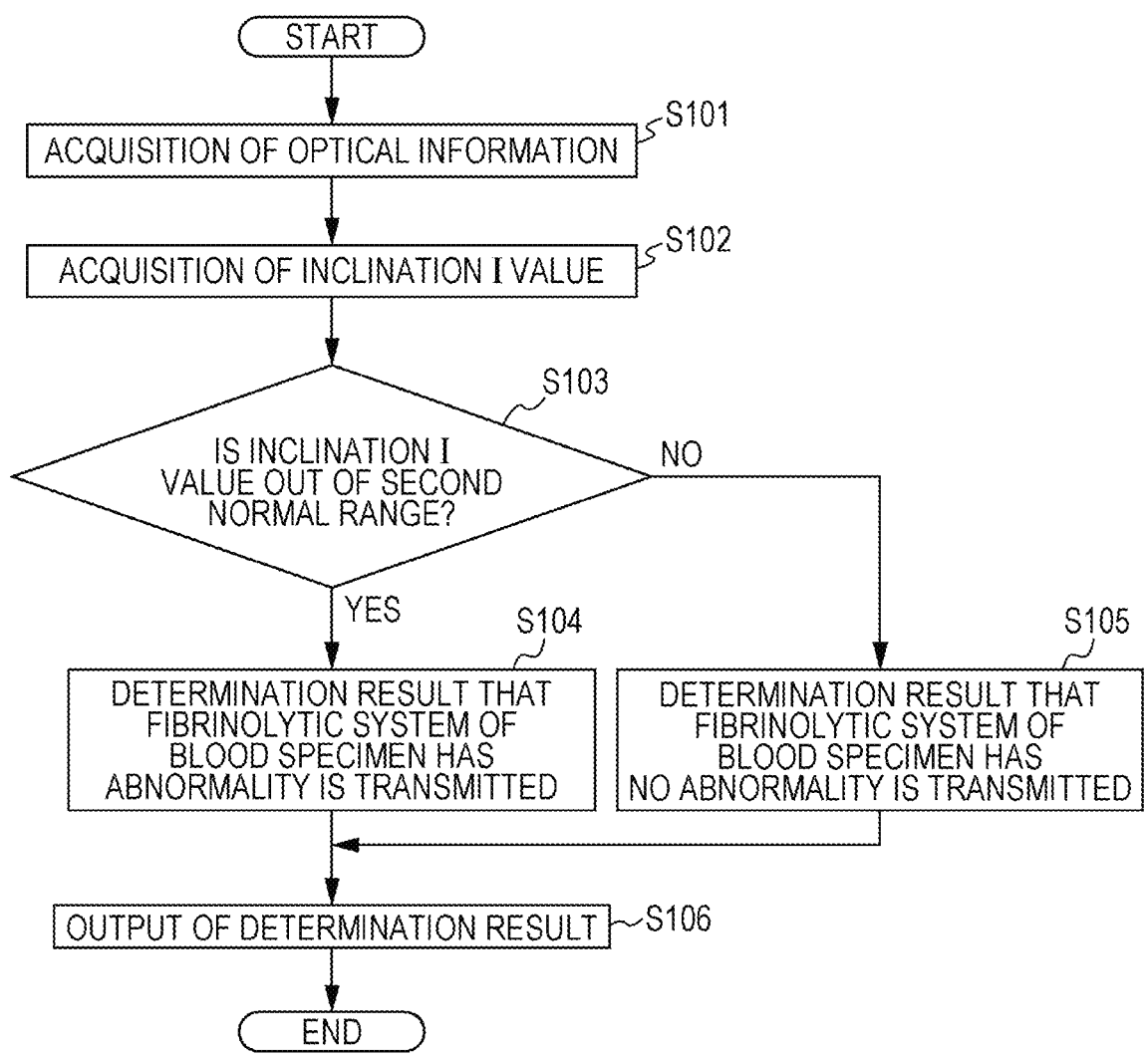
FIG. 16 is a flow chart showing the process of measuring a blood specimen by the blood specimen analyzer.

With reference to FIG. 16, the flow of the processing using one parameter regarding differentiation of the coagulation waveform is described. In this example, the inclination I value as a parameter value regarding differentiation of the coagulation waveform is acquired from the optical information on the measuring sample, and the acquired value and the second normal range are compared for acquiring information regarding the fibrinolytic capacity of the blood specimen. However, the present embodiment will not be limited to this example alone. In this example, other parameter value may be acquired in place of the inclination I for determination.

In step S101, the acquisition unit 401 of the controller 40 acquires optical information (intensity of scattered light, transmittance, or absorbance) based on the data received from the measurement unit 20 (quantity of scattered light or transmitted light). In step S102, the calculation unit 403 acquires coagulation waveform from the optical information acquired by the acquisition unit 401, and calculates the inclination I value according to the formula for calculating the parameter regarding differentiation of the coagulation waveform stored in the memory unit 402. The coagulation time and coagulation waveform are not used in the below-described determination processing, but the calculation unit 403 may further calculates the coagulation time and coagulation waveform from the optical information acquired by the acquisition unit 401.

In step S103, the determination unit 404 determines whether the inclination I value calculated by the calculation unit 403 is out of the second normal range stored in the memory unit 402. When the inclination I value is out of the second normal range, the processing proceeds to step S104. In step S104, the determination unit 404 transmits the determination result that the fibrinolytic system of the blood specimen has an abnormality to the output unit 405, as the information regarding the fibrinolytic capacity of the blood specimen. On the other hand, when the inclination I value is not out of the second normal range (more specifically, when the inclination I value within the second normal range), the processing proceeds to step S105. In step S105, the determination unit 404 transmits the determination result that the fibrinolytic system of the blood specimen has no abnormality to the output unit 405. When other parameter value is used, the value is compared with the normal range corresponding to the parameter.

In step S106, the output unit 405 outputs the determination result, and displays it on the display unit 41, or allows a printer to print it. Alternatively, the result may be outputted in a voice. This allows supply of the determination result to the user as reference information about the blood specimen.

Figure 17:
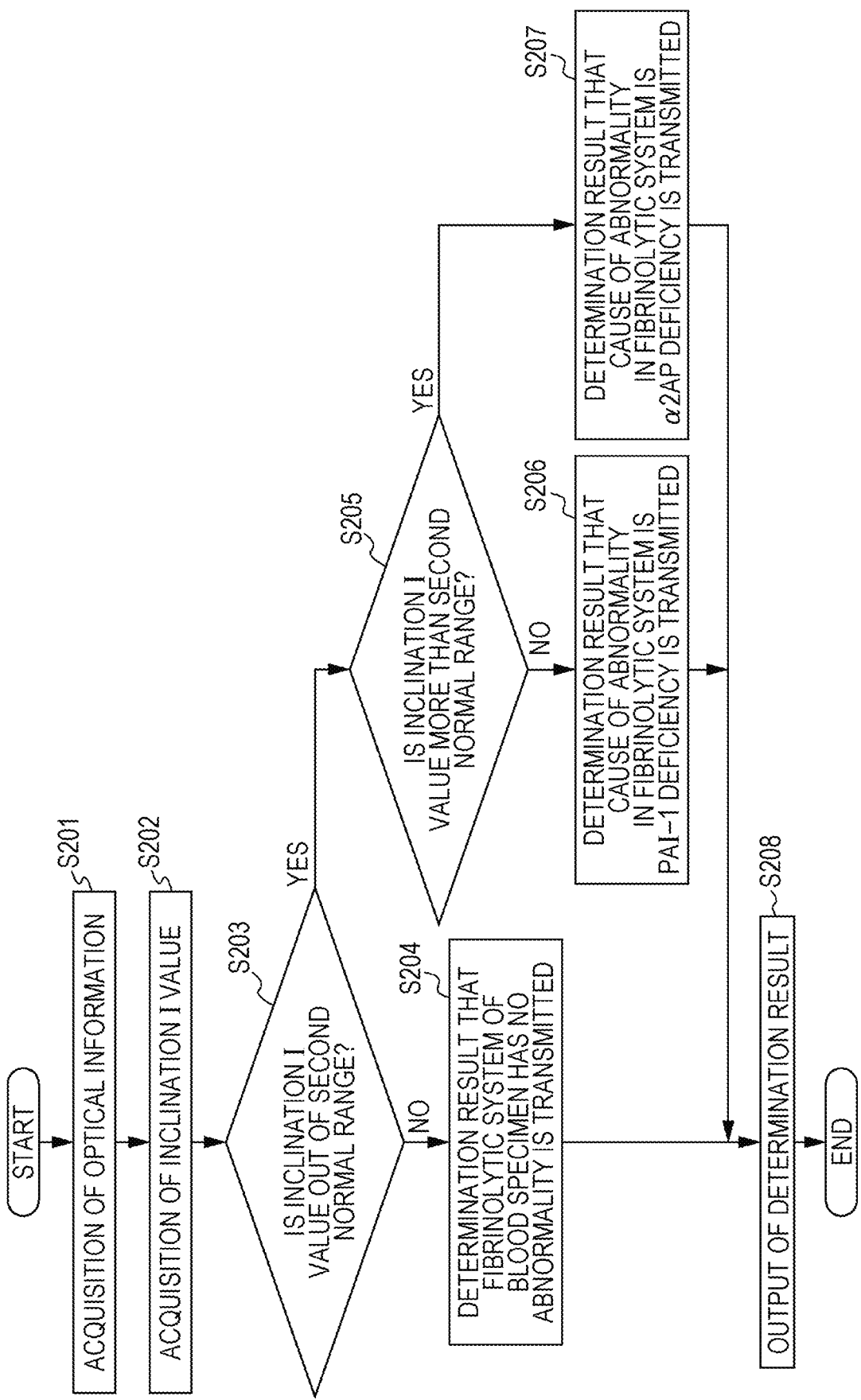
FIG. 17 is a flow chart showing the process of measuring a blood specimen by the blood specimen analyzer.

With reference to FIG. 17, the flow of the processing for acquiring information regarding the cause of abnormality in the fibrinolytic system using one parameter regarding differentiation of the coagulation waveform is described. The example described herein is the case where the inclination I value is acquired from the optical information of the measuring sample as the parameter value regarding differentiation of the coagulation waveform, the acquired value and the second normal range are compared, and the information regarding the cause of abnormality in the fibrinolytic system is acquired. However, the present embodiment will not be limited to this example alone. In this example, other parameter value may be acquired in place of the inclination I for determination.

The details about steps S201, S202, S203, and S204 are the same as those described for steps S101, S102, S103, and S105 described above. In step S203, when the inclination I value is out of the second normal range, the processing proceeds to step S205. In step S205, the determination unit 404 determines whether the inclination I value is more than the second normal range or not. When the inclination I value is not more than the second normal range (more specifically, when the inclination I value is less than the second normal range), the processing proceeds to step S206. In step S206, the determination unit 404 transmits the determination results that the fibrinolytic system of the blood specimen has an abnormality, and that the cause of abnormality is PAI-1 deficiency to the output unit 405, as the information regarding the fibrinolytic capacity of the blood specimen. On the other hand, when the inclination I value is more than the second normal range, the processing proceeds to step S207. In step S207, the determination unit 404 transmits the determination results that the fibrinolytic system of the blood specimen has an abnormality, and that the cause of abnormality is α2AP deficiency to the output unit 405, as the information regarding the fibrinolytic capacity of the blood specimen. When other parameter value is used, the value and the normal range corresponding to the parameter are compared. In this case, the determination criterion in step S205 and the result can be determined with reference to the details about the above-described method for analyzing a blood specimen.

Figure 18:
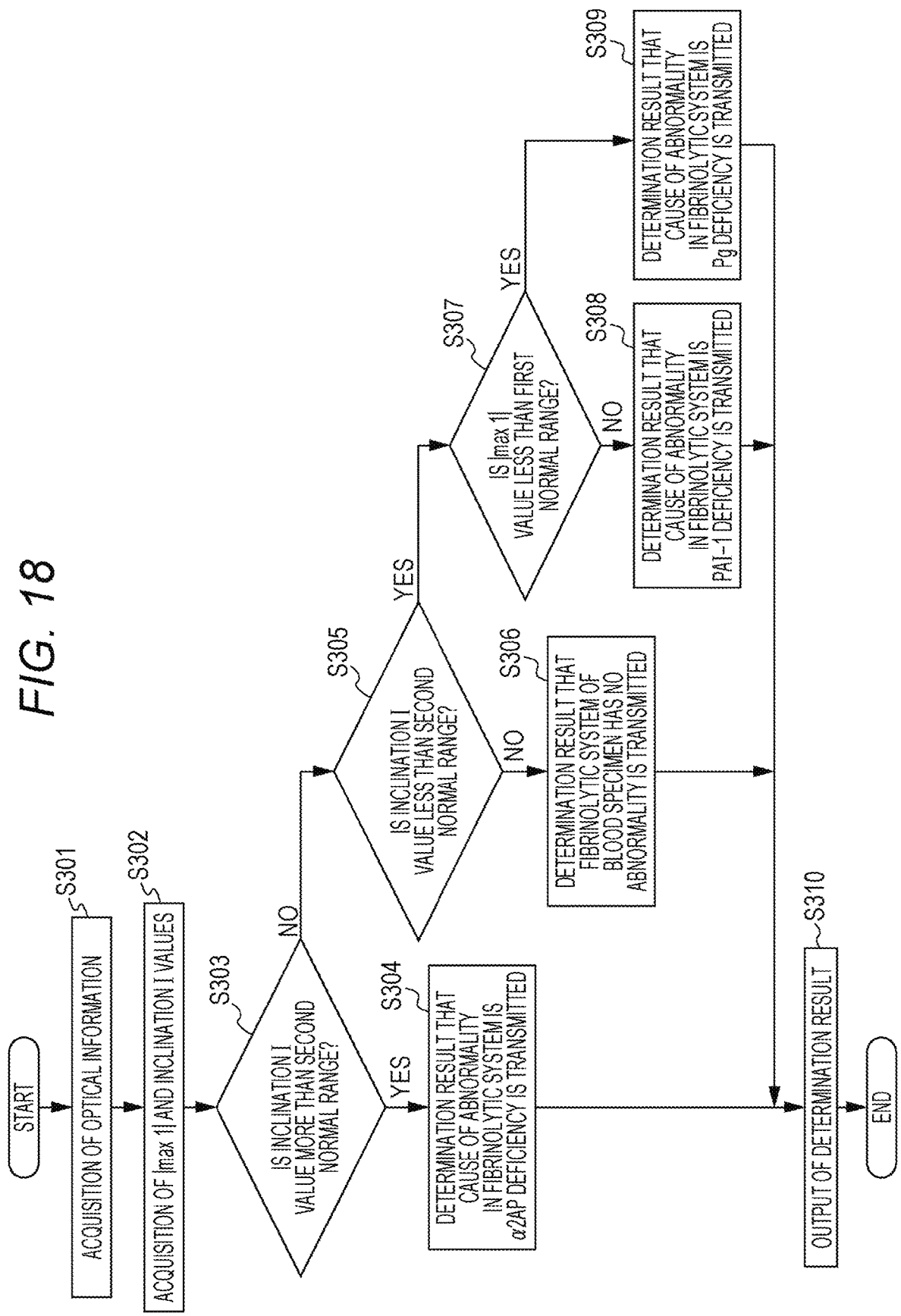
FIG. 18 is a flow chart showing the process of measuring a blood specimen by the blood specimen analyzer.

With reference to FIG. 18, the flow of the processing when using two parameters regarding differentiation of the coagulation waveform is described. The example described herein is the case where the information about whether the blood specimen is suspected of α2AP deficiency, PAI-1 deficiency or plasminogen deficiency is acquired based on the |max 1| and inclination I values as the parameter values regarding differentiation of the coagulation waveform. However, the present embodiment will not be limited to this example alone.

The details about step S301 are the same as those described for step S101 described above. In step S302, the calculation unit 403 acquires a coagulation waveform from the optical information acquired by the acquisition unit 401, and calculates the |max 1| and inclination I values according to the formula for calculating the parameter regarding differentiation of the coagulation waveform stored in the memory unit 402. The calculation unit 403 may further calculate the coagulation time and coagulation waveform.

In step S303, the determination unit 404 determines whether the inclination I value is more than the second normal range. When the inclination I value is more than the second normal range, the processing proceeds to step S304. In step S304, the determination unit 404 transmits the determination results that the fibrinolytic system of the blood specimen has an abnormality, and that the cause of the abnormality is α2AP deficiency to the output unit 405, as the information regarding the fibrinolytic capacity of the blood specimen. On the other hand, when the inclination I value is not more than the second normal range, the processing proceeds to step S305.

In step S305, the determination unit 404 determines whether the inclination I value is less than the second normal range. When the inclination I value is not less than the second normal range (more specifically, when the inclination I value is within the second normal range), the processing proceeds to step S306. In step S306, the determination unit 404 transmits the determination result that the fibrinolytic system of the blood specimen has no abnormality to the output unit 405, as the information regarding the fibrinolytic capacity of the blood specimen. On the other hand, when the inclination I value is less than the second normal range, the processing proceeds to step S307.

In step S307, the determination unit 404 determines whether the |max 1| value is less than the first normal range.

When the inclination I value is not less than the second normal range (more specifically, when the |max 1| value is within or more than the first normal range), the processing proceeds to step S308. In step S308, the determination unit 404 transmits the determination results that the fibrinolytic system of the blood specimen has an abnormality, and that the cause of the abnormality is PAI-1 deficiency to the output unit 405, as the information regarding the fibrinolytic capacity of the blood specimen. On the other hand, when the |max 1| value is less than the first normal range, the processing proceeds to step S309. In step S309, the determination unit 404 transmits the determination results that the fibrinolytic system of the blood specimen has an abnormality, and that the cause of the abnormality is plasminogen (Pg) deficiency to the output unit 405, as the information regarding the fibrinolytic capacity of the blood specimen.

Figure 19:
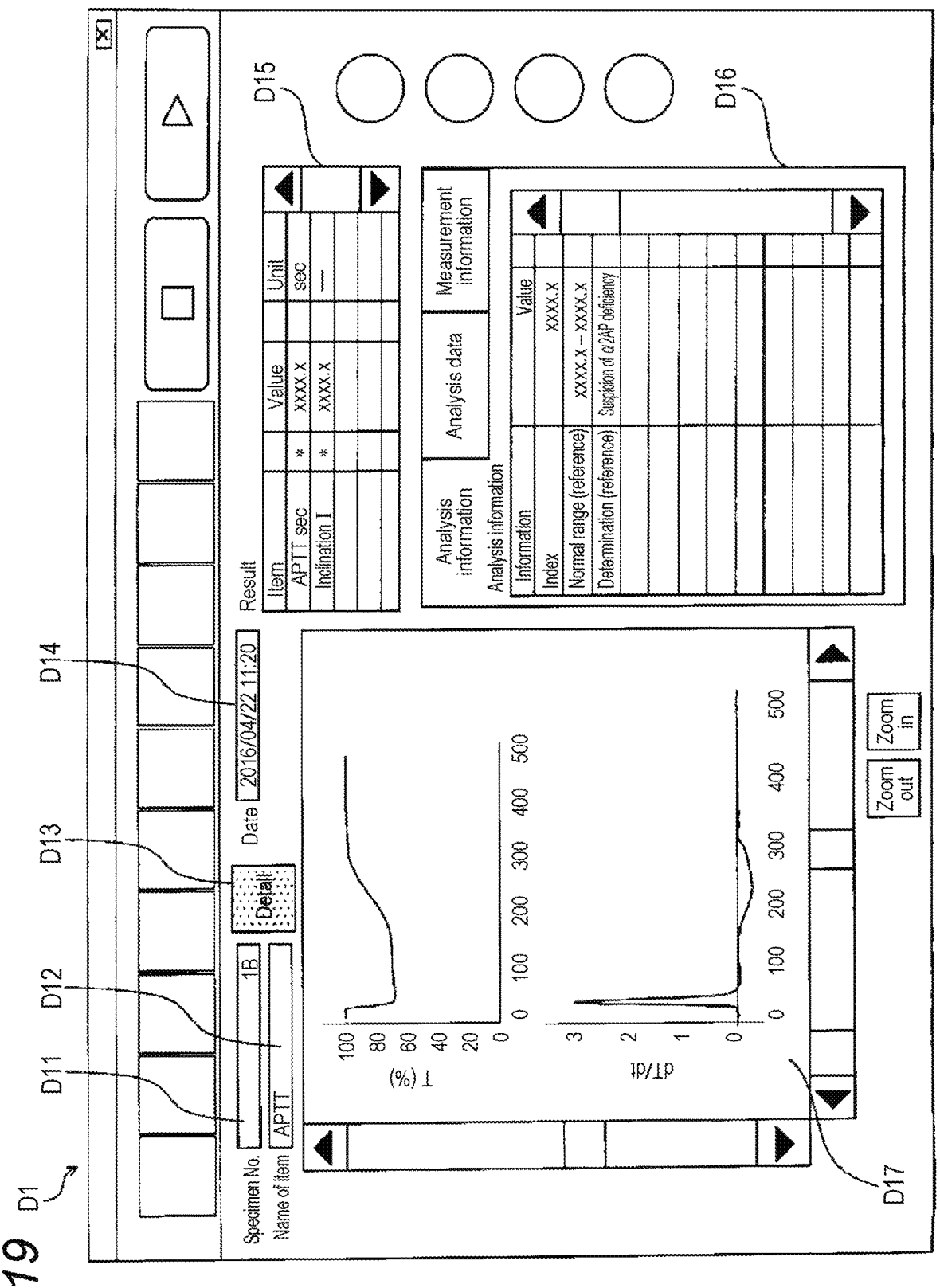
FIG. 19 shows an example of a screen displaying analysis results by a blood specimen analyzer.

As an example of the screen displaying the analysis result, with reference to FIG. 19, the screen displaying the result of the analysis of a series of steps from coagulation through fibrinolysis of the blood specimen using an activating agent for fibrinolytic system, a reagent for measuring APTT, and a calcium solution is described. A screen D1 includes a region D11 for displaying the specimen number, a region D12 for displaying the name of measurement item, a button D13 for displaying the detail screen, a region D14 for displaying the date of measurement, a region D15 for displaying the measurement result, a region D16 for displaying the analysis information, and a region D17 for displaying the coagulation waveform and the graph showing differentiation of the waveform.

The region D15 displays the measurement item and measurement value. In the region D15, "APTT sec" is the time of activated partial thromboplastin time. The region D15 may also display the parameter values regarding differentiation of the coagulation waveform, such as the inclination I, inclination II, and |Max1|.

The region D16 displays the analysis item and reference information. In the region D16, "Index" is the parameter value regarding differentiation of the coagulation waveform used for the determination. The "normal range (reference)" is the normal range corresponding to the parameter value used for the determination. The "determination (reference)" is the determination result by the blood specimen analyzer. FIG. 19 shows that the blood specimen is a specimen suspected of having α2AP deficiency. The diagnosis of the abnormality in the fibrinolytic system preferably considers information of other test results, in addition to the result of this determination. Accordingly, in order to show that the determination result and normal range by the blood specimen analyzer according to the present embodiment are reference information, there are annotations "(reference)". In FIG. 19, the determination result is shown by the letters "suspicion of α2AP deficiency", but it may be shown by a symbol such as a flag, or a graphic mark. Alternatively, the determination result may be outputted in a voice.

The present invention will be described below in more detail by way of Examples, but the present invention is not be limited to Examples.

EXAMPLES

Example 1: Analysis of α2-Anti Plasmin (α2AP)-Deficient Specimen (1) Reagent and Measuring Apparatus An APTT measurement reagent, APTT-SLA (Sysmex Corporation) was used as a reagent for measuring a coagulation time. A 20 mM calcium chloride solution (Sysmex Corporation) was used as an aqueous solution containing calcium ions. In the present example, a tissue-type plasminogen activator (product name "ACTIVACIN", Kyowa Hakko Kirin Co., Ltd.) as an activating agent for fibrinolytic system was added to the 20 mM calcium chloride solution at a final concentration of 0.625 μg/mL (10.09 nM). The coagulation waveform data of a measuring sample was acquired using a full automatic blood coagulation measuring apparatus (product name "CS-2000i", Sysmex Corporation).

(2) Blood Plasma Subject

Normal blood plasma (autologous preparation) and α2AP-deficient blood plasma (Affinity Biologicals Inc.) were mixed at volume ratios of 10:0, 3:7, 1:9, and 0:10, thereby obtaining blood plasma subjects. According to the proportion of the normal blood plasma in these blood plasma subjects, the prepared blood plasma subjects are referred to as 100% α2AP, 30% α2AP, 10% α2AP, and 0% α2AP, respectively.

(3) Measurement

Each of the blood plasma subjects was dispensed into a reaction cuvette in portion of 50 μL, and warmed at 37° C. for 1 minute. The APTT reagent (50 μL), which had been warmed at 37° C. in advance, was added to the reaction cuvette in portion of 50 μL, mixed, and allowed to react at 37° C. for 3 minutes. After the reaction, a t-PA-containing 20 mM calcium chloride solution was added to the mixtures in portion of 50 μL, and mixed, thereby obtaining a measuring sample (final concentration of t-PA: 0.21 μg/mL). The transmittance of the measuring sample was continuously measured for 500 seconds from the time point of addition of the above-described calcium chloride solution.

(4) Analysis and Results

Figure 3A:
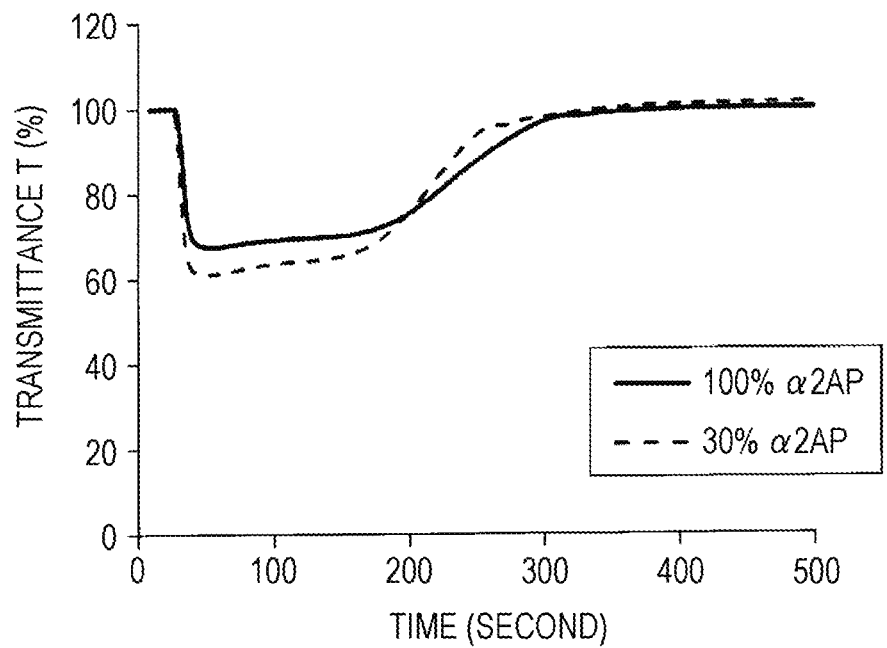
FIG. 3A is a coagulation waveform obtained by measuring the transmittance of measuring samples prepared from normal blood plasma and α2AP-deficient blood plasma (30% α2AP), respectively.
Figure 3B:
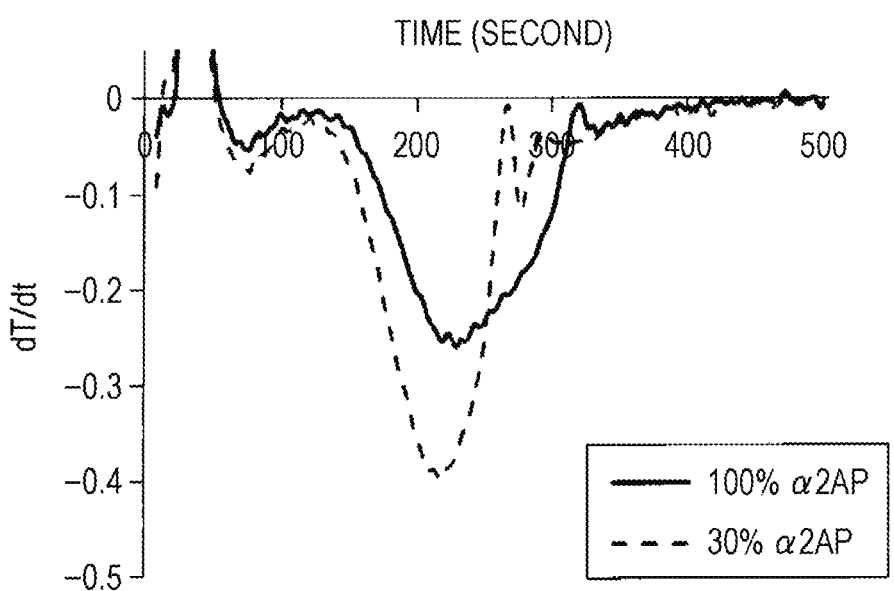
FIG. 3B is a rate waveform obtained by primary differentiation of the coagulation waveform of FIG. 3A.

A time-dependent change in the transmittance was plotted to obtain a coagulation waveform. In addition, the data of the coagulation waveform was subjected to primary differentiation to obtain rate waveform data. Among them, the coagulation waveform and rate waveform of 100% α2AP and 30% α2AP are shown in FIGS. 3A and B, respectively. In FIG. 3B, the portion where the ordinate (rate) is negative is enlarged. From each waveform data, parameters shown in Table 1 were acquired. In Table 1, the time shown together with the |max1| value is the time reaching the maximum fibrinolysis rate from the initiation of the measurement.

TABLE 1

| α2AP (%) | Coagulation time (seconds) | |max 1| | Inclination I | Inclination II | Area | FL time (seconds) | Starting point of fibrinolysis (seconds) | End point of fibrinolysis (seconds) |
|---|---|---|---|---|---|---|---|---|
| 100 | 33.1 | 0.260 (228.9 seconds) | 0.00684 | 0.00171 | 26.6 | 204.4 | 115.8 | 320.2 |
| 30 | 31.2 | 0.401 (217.3 seconds) | 0.01774 | 0.00513 | 29.3 | 146.2 | 120.1 | 266.3 |

TABLE 1-continued

| α2AP (%) | Coagulation time (seconds) | \|max 1\| | Inclination I | Inclination II | Area | FL time (seconds) | Starting point of fibrinolysis (seconds) | End point of fibrinolysis (seconds) |
|---|---|---|---|---|---|---|---|---|
| 10 | 31.0 | 0.452 (215.6 seconds) | 0.01977 | 0.00756 | 32.6 | 144.2 | 112.2 | 256.4 |
| 0 | 31.1 | 0.488 (205.8 seconds) | 0.02396 | 0.00766 | 33.2 | 136.1 | 110.2 | 246.3 |

As shown by the coagulation waveform in FIG. 3A, for both of 100% α2AP and 30% α2AP, the transmittance decreased by coagulation, and then increased after some time. Such a change in the waveform was observed also for 10% α2AP and 0% α2AP. These facts indicate that fibrinolysis started after completion of coagulation of the blood plasma subject. As shown in FIG. 3B and Table 1, a tendency was observed that the higher the proportion of the α2AP-deficient blood plasma in the blood plasma subject is, the higher the \|max 1\|, inclination I, inclination II, and area values are. On the other hand, a tendency was observed that the higher the proportion of the α2AP-deficient blood plasma in the blood plasma subject is, the shorter the FL time is.

Accordingly, these facts showed that the parameters regarding differentiation of the coagulation waveform acquired from a blood plasma subject containing α2AP-deficient blood plasma are different from the parameters acquired from normal blood plasma, and have a characteristic tendency. Accordingly, it was suggested that the analysis method of the present embodiment can analyze whether the blood plasma subject has an abnormality in the fibrinolytic system. For example, whether the cause of abnormality in the fibrinolytic system is α2AP or not can be determined by using the parameter value regarding differentiation of the coagulation waveform obtained from normal blood plasma as the cutoff value.

Example 2: Analysis of Plasminogen Activator Inhibitor 1 (PAI-1)-Deficient Specimen (1) Reagent, Measuring Apparatus, and Measurement A reagent for measuring a coagulation time, an activating agent for fibrinolytic system, and a measuring apparatus were the same as those used in Example 1. A measuring sample was prepared, and coagulation waveform data were acquired in the same manner as in Example 1, except that the below-described blood plasma subjects were used as blood specimens.

(2) Blood Plasma Subject

Normal blood plasma (autologous preparation) and PAI-1-deficient blood plasma (Affinity Biologicals Inc.) were mixed at volume ratios of 10:0, 9:1, 7:3, 3:7, 1:9, and 0:10, thereby obtaining blood plasma subjects. According to the proportion of the normal blood plasma in these blood plasma subjects, the prepared blood plasma subjects are referred to as 100% PAI-1, 90% PAI-1, 70% PAI-1, 30% PAI-1, 10% PAI-1, and 0% PAI-1, respectively. The 100% PAI-1 and 0% PAI-1 were prepared duplicate.

(3) Analysis and Results

Figure 4A:
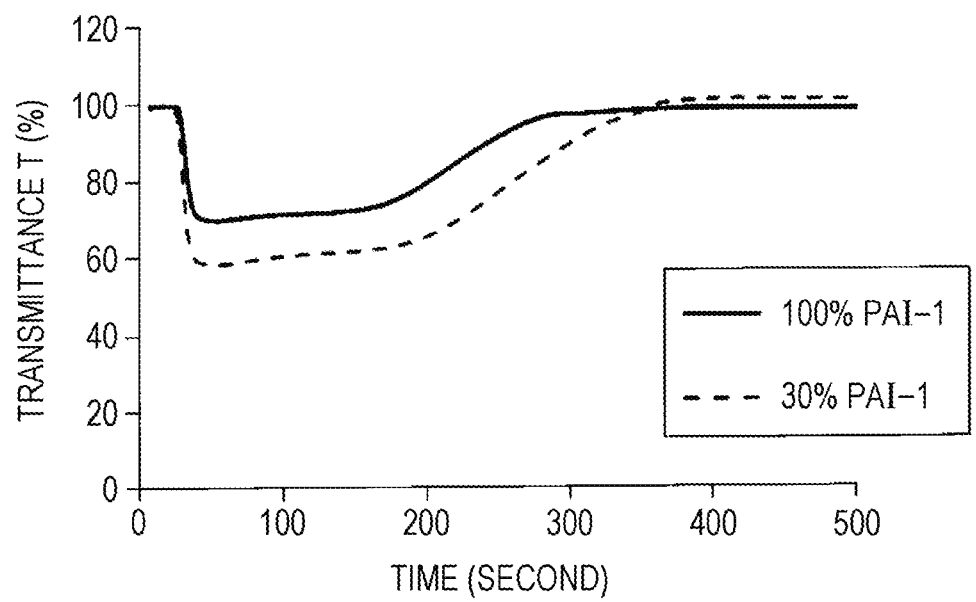
FIG. 4A is a coagulation waveform obtained by measuring the transmittance of measuring samples prepared from normal blood plasma and PAI-1-deficient blood plasma (30% PAI-1), respectively.
Figure 4B:
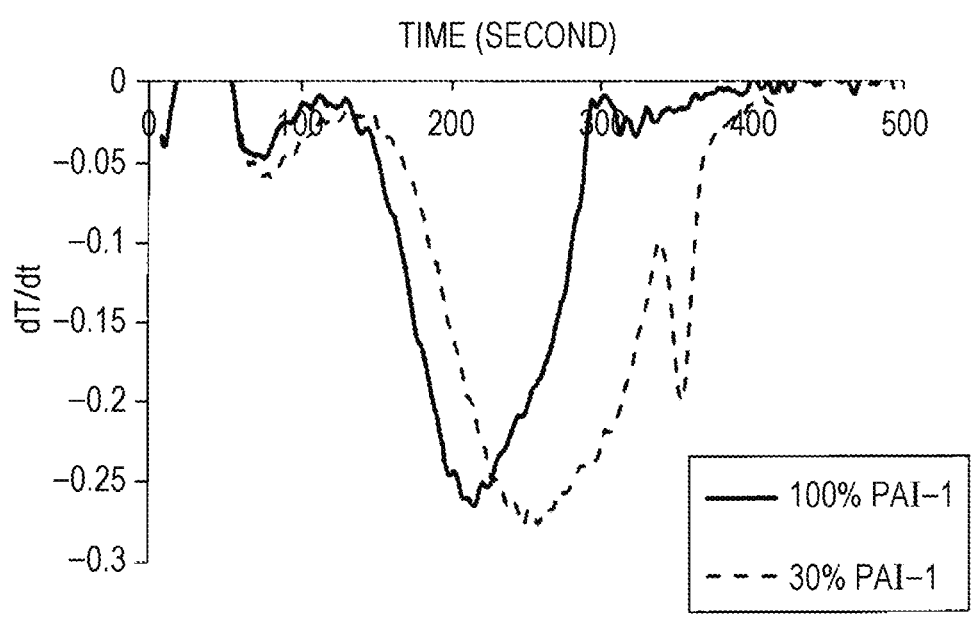
FIG. 4B is a rate waveform obtained by primary differentiation of the coagulation waveform of FIG. 4A.

A time-dependent change in the transmittance was plotted to obtain a coagulation waveform. In addition, the data of the coagulation waveform was subjected to primary differentiation to obtain the rate waveform data. Among them, the coagulation waveform and rate waveform of 100% PAI-1 and 30% PAI-1 are shown in FIGS. 4A and B, respectively. In FIG. 4B, the portion where the ordinate (rate) is negative is enlarged. From each waveform data, parameters shown in Table 2 were acquired. In Table 2, the time shown together with the \|max1\| value is the time reaching the maximum fibrinolysis rate from the initiation of the measurement.

TABLE 2

| PAI-1 (%) | Coagulation time (seconds) | \|max 1\| | Inclination I | Inclination II | Area | FL time (seconds) | Starting point of fibrinolysis (seconds) | End point of fibrinolysis (seconds) |
|---|---|---|---|---|---|---|---|---|
| 100 | 32.5 | 0.266 (215.4 seconds) | 0.00644 | 0.00210 | 25.3 | 190.1 | 111.8 | 301.9 |
| 100 | 33.0 | 0.260 (218.4 seconds) | 0.00662 | 0.00202 | 24.3 | 187.4 | 114.8 | 302.2 |
| 90 | 32.1 | 0.265 (228.0 seconds) | 0.00609 | 0.00192 | 24.6 | 185.8 | 126.4 | 312.2 |
| 70 | 31.4 | 0.271 (238.9 seconds) | 0.00526 | 0.00165 | 26.5 | 195.3 | 126.2 | 321.5 |
| 30 | 31.2 | 0.278 (248.0 seconds) | 0.00448 | 0.00118 | 29.0 | 208.5 | 130.1 | 338.6 |
| 10 | 31.4 | 0.274 (257.7 seconds) | 0.00444 | 0.00103 | 28.2 | 206.2 | 139.7 | 345.9 |
| 0 | 31.5 | 0.275 (272.7 seconds) | 0.00361 | 0.00087 | 31.3 | 227.4 | 146.2 | 373.6 |
| 0 | 31.3 | 0.280 (270.6 seconds) | 0.00342 | 0.00092 | 31.2 | 223.3 | 132.9 | 356.2 |

As shown by the coagulation waveform in FIG. 4A, for both of 100% PAI-1 and 30% PAI-1, the transmittance decreased by coagulation, and then increased after some time. Such a change in the waveform was observed also for the remaining blood plasma subjects. These facts indicate that fibrinolysis started after completion of coagulation of the blood plasma subject. As shown in FIG. 4B and Table 2, a tendency was observed that the higher the proportion of the PAI-1-deficient blood plasma in the blood plasma subject is, the longer the FL time is. The area value seemed to increase with an increase in the proportion of the PAI-1-deficient blood plasma in the blood plasma subject. On the other hand, a tendency was observed that the higher the proportion of the PAI-1-deficient blood plasma in the blood plasma subject is, the lower the inclination I and inclination II values are. There was no significant change in the |max 1| value between the blood plasma subjects, but the time reaching the maximum fibrinolysis rate was longer with an increase in the proportion of the PAI-1-deficient blood plasma in the blood plasma subject.

Accordingly, these facts showed a tendency that the parameters regarding differentiation of the coagulation waveform acquired from a blood plasma subject containing PAI-1-deficient blood plasma are different from the parameters acquired from normal blood plasma, and have a characteristic tendency. Accordingly, it was suggested that the analysis method of the present embodiment can analyze whether the blood plasma subject has an abnormality in the fibrinolytic system. For example, whether the cause of abnormality in the fibrinolytic system is PAI-1 or not can be determined by using the parameter value regarding differentiation of the coagulation waveform obtained from normal blood plasma as the cutoff value.

Example 3: Analysis of Plasminogen (Pg)-Deficient Specimen (1) Reagent, Measuring Apparatus and Measurement A reagent for measuring a coagulation time, an activating agent for fibrinolytic system, and a measuring apparatus were the same as those used in Example 1. A measuring sample was prepared, and coagulation waveform data were acquired in the same manner as in Example 1, except that the below-described blood plasma subjects were used as blood specimens.

(2) Blood Plasma Subject

Normal blood plasma (autologous preparation) and Pg-deficient blood plasma (Affinity Biologicals Inc.) were mixed at volume ratios of 10:0, 3:7, 1:9, and 0:10, thereby obtaining blood plasma subjects. According to the proportion of the normal blood plasma in these blood plasma subjects, the prepared blood plasma subjects are referred to as 100% Pg, 30% Pg, 10% Pg, and 0% Pg, respectively.

(3) Analysis and Results

Figure 5A:
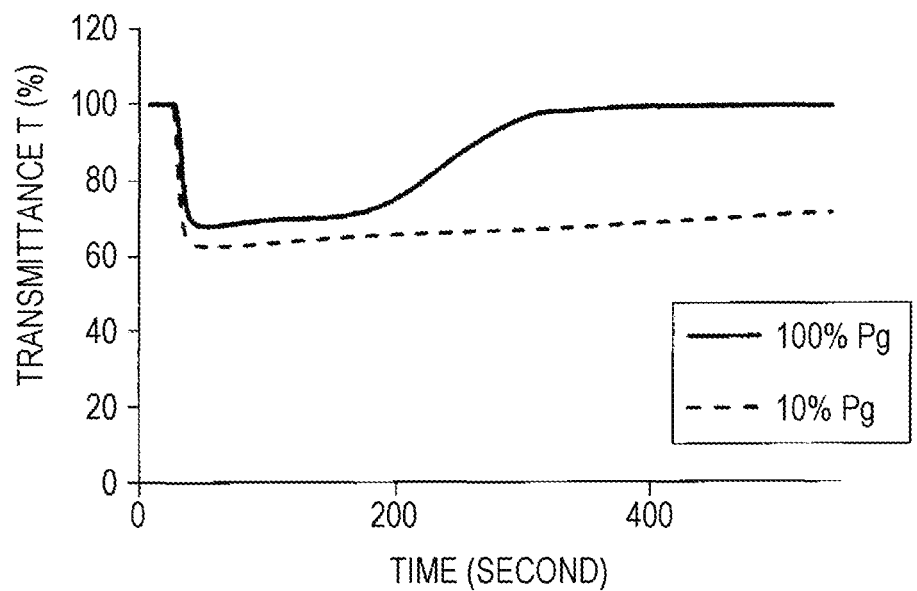
FIG. 5A is a coagulation waveform obtained by measuring the transmittance of measuring samples prepared from normal blood plasma and plasminogen-deficient blood plasma (10% Pg), respectively.
Figure 5B:
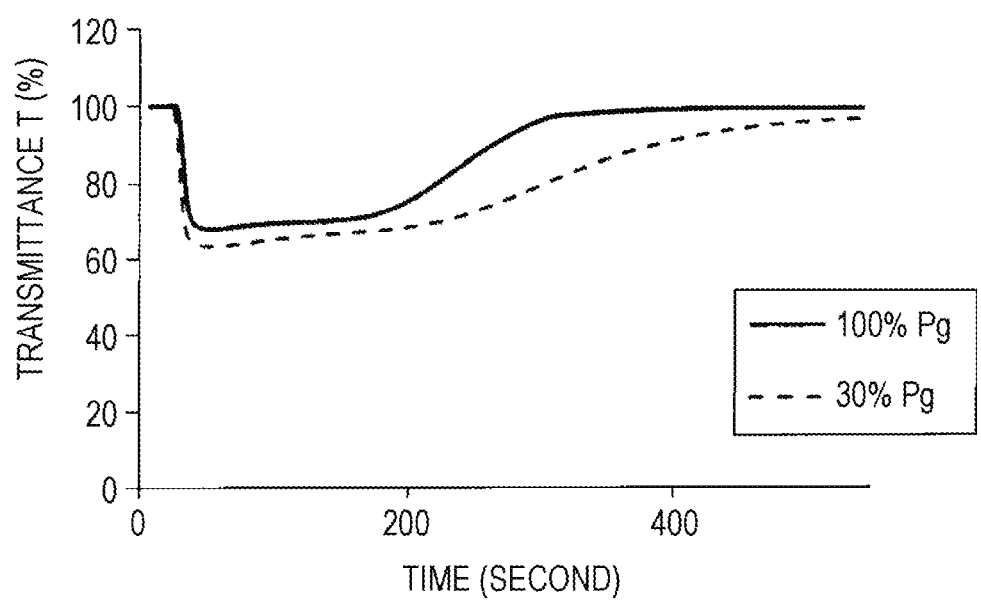
FIG. 5B is a coagulation waveform obtained by measuring the transmittance of measuring samples prepared from normal blood plasma and plasminogen-deficient blood plasma (30% Pg), respectively.
Figure 5C:
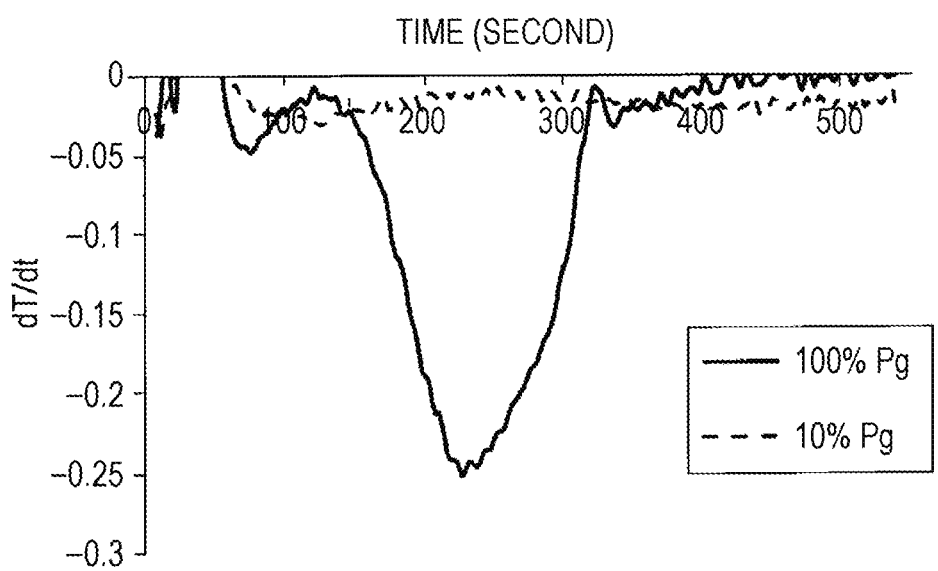
FIG. 5C is a rate waveform obtained by primary differentiation of the coagulation waveform of FIG. 5A.

A time-dependent change in the transmittance was plotted to obtain a coagulation waveform. In addition, the data of the coagulation waveform was subjected to primary differentiation to obtain the rate waveform data. Among them, the coagulation waveforms of 100% Pg, 30% Pg, and 10% Pg are shown in FIGS. 5A and B, respectively. The rate waveforms of 100% Pg, 30% Pg, and 10% Pg are shown in FIGS. 5C and D, respectively. In FIGS. 5C and D, the portion where the ordinate (rate) is negative is enlarged. From each waveform data, the parameters shown in Table 3 were acquired. In Table 3, the time shown together with the |max1| value is the time reaching the maximum fibrinolysis rate from the initiation of the measurement. In Table 3, "–" represents that no parameter could not be acquired.

TABLE 3

| Pg (%) | Coagulation time (seconds) | |max 1| | Inclination I | Inclination II | Area | FL time (seconds) | Starting point of fibrinolysis (seconds) | End point of fibrinolysis (seconds) |
|---|---|---|---|---|---|---|---|---|
| 100 | 33.2 | 0.252 (227.3 seconds) | 0.00585 | 0.00175 | 25.6 | 203.2 | 120.7 | 323.9 |
| 30 | 31.9 | 0.125 (308.8 seconds) | — | 0.00060 | 23.4 | — | 164.2 | — |
| 10 | 30.8 | — | — | — | — | — | 254.0 | — |
| 0 | 30.9 | — | 0 | 0 | — | — | — | — |

As shown by the coagulation waveforms in FIGS. 5A and B, for 100% Pg, the transmittance decreased by coagulation, and then increased after some time. As shown in FIG. 5A, for 10% Pg, the transmittance decreased by coagulation, and scarcely increased thereafter. Such a change in the waveform was observed also for 0% Pg. As shown in FIG. 5B, for 30% Pg, the transmittance decreased by coagulation, and increased thereafter, but did not return to 100% during the measurement time. Accordingly, for 30% Pg, 10% Pg, and 0% Pg, the end point of fibrinolysis could not be determined, and the FL time could not be acquired. Such a coagulation waveform is specific to Pg-deficient blood plasma, it is thus suggested that the coagulation waveform allows the analysis that the fibrinolytic system has an abnormality and its cause is Pg.

Figure 5D:
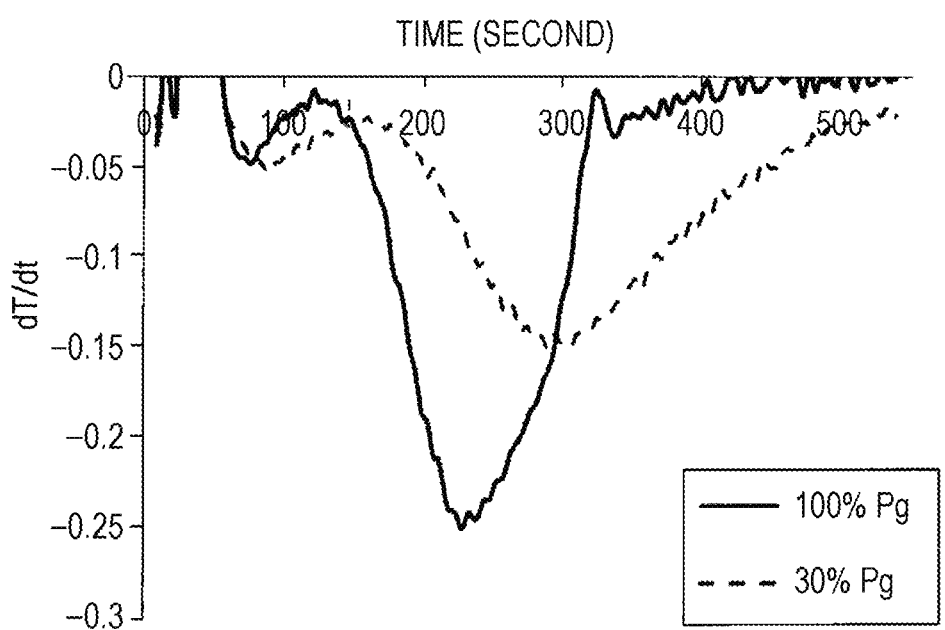
FIG. 5D is a rate waveform obtained by primary differentiation of the coagulation waveform of FIG. 5B.

As shown in FIG. 5C, for 10% Pg, there was almost no change in the rate after completion of coagulation. Such a change in the waveform was also observed for 0% Pg. Accordingly, for 10% Pg and 0% Pg, the |max 1|, area, inclination I, and inclination II values could not be acquired. As shown in FIG. 5D, for 30% Pg, a tendency was observed that the |max 1| and inclination II values are lower than those for 100% Pg. On the other hand, for 30% Pg, a tendency was observed that the time reaching the maximum fibrinolysis rate is longer than that for 100% Pg. FIGS. 5C and D indicate that, for the Pg-deficient blood plasma, the peak by fibrinolysis tends to disappear in the rate waveform. Accordingly, for the Pg-deficient specimen, the inclination I and inclination II values are expected to approach 0. More specifically, for the Pg-deficient specimen, the inclination I and inclination II values are expected to be lower than those for the normal blood plasma. As described above, it was observed that the parameters regarding differentiation of the coagulation waveform acquired from the blood plasma subject containing Pg-deficient blood plasma are different from the parameters acquired from the normal blood plasma, and have a characteristic tendency. Such a waveform of primary differentiation is specific to the Pg-deficient blood plasma, it is thus suggested that the waveform of primary differentiation allows the analysis that the fibrinolytic system has an abnormality and its cause is Pg.

The above facts suggest that the analysis method of the present embodiment can analyze whether a blood plasma subject has abnormality in the fibrinolytic system. For example, whether the cause of abnormality in the fibrinolytic system is Pg or not can be determined by using the parameter value regarding differentiation of the coagulation waveform acquired from normal blood plasma as the cutoff value.

What is claimed is:

1. A method for analyzing a blood specimen, comprising the steps of:
 mixing the blood specimen with a reagent containing an activating agent for a fibrinolytic system, and obtaining optical properties that are proportional to a formation and a decomposition of a fibrin clot in the blood specimen to acquire a coagulation waveform;
 acquiring at least two parameter values regarding differentiation of the coagulation waveform, the parameter value being obtained from a rate waveform that is obtained by primary differentiation of the coagulation waveform with respect to time by using a processor; and
 identifying, based on the parameter values, a cause of abnormality in the fibrinolytic system of the blood specimen, the cause being selected from α2-antiplasmin (α2AP) deficiency, plasminogen activator inhibitor-1 (PAI-1) deficiency and, plasminogen deficiency,
 wherein the optical properties are detected by irradiating a measuring sample with light, and
 wherein the at least two parameter values are selected from the group consisting of a maximum fibrinolysis rate, an inclination I, an inclination II, a FL time, an area, and a time of reaching the maximum fibrinolysis rate.

2. The method according to claim 1, wherein the coagulation waveform is obtained from the measuring sample comprising the blood specimen, the reagent containing the activating agent for the fibrinolytic system, a reagent for measuring a coagulation time, and calcium ions.

3. The method according to claim 1, wherein the optical properties comprise a scattered light amount, transmittance, or absorbance, each measured continuously or intermittently, and the coagulation waveform shows a time-dependent change in the scattered light amount, transmittance, or absorbance.

4. The method according to claim 1, wherein the identifying step comprises the following steps performed by using the processor:
 comparing the parameter values with reference value ranges obtained from a subject who does not have an abnormality in the fibrinolytic system; and
 identifying the cause of the abnormality in the fibrinolytic system of the blood specimen as any one of α2AP deficiency, PAI-1 deficiency and plasminogen deficiency when at least one of the parameter values is outside the reference value range.

5. The method according to claim 4, wherein when a |max 1| value is acquired as one of the parameter values, the following steps are performed by using the processor:
 comparing, the maximum fibrinolysis rate value with the reference value range obtained from the subject who does not have the abnormality in the fibrinolytic system;
 identifying the cause of the abnormality in the fibrinolytic system of the blood specimen as α2AP deficiency when the maximum fibrinolysis rate value is higher than an upper limit of the reference value range; and
 identifying the cause of the abnormality in the fibrinolytic system of the blood specimen as plasminogen deficiency when the maximum fibrinolysis rate value is lower than a lower limit of the reference value range.

6. The method according to claim 4, wherein when an inclination I value is acquired as one of the parameter values, the following steps are performed by using the processor:
 comparing the inclination I value with the reference value range obtained from the subject who does not have the abnormality in the fibrinolytic system;
 identifying the cause of the abnormality in the fibrinolytic system of the blood specimen as α2AP deficiency when the inclination I value is higher than an upper limit of the reference value range; and
 identifying the cause of the abnormality in the fibrinolytic system of the blood specimen as PAI-1 deficiency when the inclination I value is lower than a lower limit of the reference value range.

7. The method according to claim 4, wherein when an inclination II value is acquired as one of the parameter values, the following steps are performed by using the processor:
 comparing the inclination II value with the reference value range obtained from the subject who does not have the abnormality in the fibrinolytic system;
 identifying the cause of the abnormality in the fibrinolytic system of the blood specimen as α2AP deficiency when the inclination II value is higher than an upper limit of the reference value range; and
 identifying the cause of the abnormality in the fibrinolytic system of the blood specimen as PAI-1 or plasminogen deficiency when the inclination II value is lower than a lower limit of the reference value range.

8. The method according to claim 4, wherein when an FL time value is acquired as one of the parameter values, the following steps are performed by using the processor:
 comparing the FL time value with the reference value range obtained from the subject who does not have the abnormality in the fibrinolytic system;
 identifying the cause of the abnormality in the fibrinolytic system of the blood specimen as PAI-1 deficiency when the FL time value is higher than an upper limit of the reference value range; and
 identifying the cause of the abnormality in the fibrinolytic system of the blood specimen as α2AP deficiency when the FL time value is lower than a lower limit of the reference value range.

9. The method according to claim 4, wherein when an area value is acquired as one of the parameter values, the following steps are performed by using the processor:
 comparing the area value with the reference value range obtained from the subject who does not have the abnormality in the fibrinolytic system; and
 identifying the cause of the abnormality in the fibrinolytic system of the blood specimen as α2AP or PAI-1 deficiency when the area value is lower than a lower limit of the reference value range.

10. The method according to claim 4, wherein when a time reaching the maximum fibrinolysis rate value is acquired as one of the parameter values, the following steps are performed by using the processor:

comparing the time reaching the maximum fibrinolysis rate value with the reference value range obtained from the subject who does not have the abnormality in the fibrinolytic system; and identifying the cause of the abnormality in the fibrinolytic system of the blood specimen as PAI-1 or plasminogen deficiency when the time reaching the maximum fibrinolysis rate value is higher than an upper limit of the reference value range.

11. The method according to claim 1, wherein when a |max 1| value and an inclination I value are acquired as the parameter values, the following steps are performed by using the processor:

comparing the inclination I value with a first reference value range obtained from a subject who does not have the abnormality in the fibrinolytic system, and identifying the cause of the abnormality in the fibrinolytic system of the blood specimen as α2AP deficiency when the inclination I value is higher than an upper limit of the first reference value range;

comparing the maximum fibrinolysis rate value with a second reference value range obtained from the subject who does not have the abnormality in the fibrinolytic system when the inclination I value is lower than a lower limit of the first reference value range, and identifying the cause of the abnormality in the fibrinolytic system of the blood specimen as plasminogen deficiency when the maximum fibrinolysis rate value is lower than a lower limit of the second reference value range, and identifying the cause of the abnormality in the fibrinolytic system of the blood specimen as PAI-1 deficiency when the maximum fibrinolysis rate value is within the second reference value range or higher than an upper limit of the second reference value range.

12. The method according to claim 1, which further comprises:

preparing the measuring sample by the steps of: mixing the blood specimen with a reagent for measuring a coagulation time containing a phospholipid and the reagent containing the activating agent for a coagulation system; and mixing a resulting mixture with an aqueous solution containing the activating agent for the fibrinolytic system and calcium ions.

13. The method according to claim 1, wherein the identifying step comprises the following step performed by using the processor;

comparing the parameter values obtained from the blood specimen with reference value ranges stored in a memory, the reference value ranges being obtained from a subject who does not have an abnormality in the fibrinolytic system.

14. The method according to claim 1, which further comprises:

displaying the coagulation waveform, the rate waveform and a result of the identifying step on a screen by using the processor.

* * * * *